US009896652B2

United States Patent
Ashley et al.

(10) Patent No.: US 9,896,652 B2
(45) Date of Patent: Feb. 20, 2018

(54) PHOTOBIOREACTOR, SYSTEM AND METHOD OF USE

(71) Applicant: Algenol Biofuels Switzerland GmbH, Zug (CH)

(72) Inventors: Oliver Ashley, Fort Myers, FL (US); William M. Drake, II, Fort Myers, FL (US); Omatoyo Kofi Dalrymple, Fort Myers, FL (US); Edwin Malkiel, Naples, FL (US); Robert Paul Woods, Naples, FL (US); Jason Keith Ward, Estero, FL (US); Kevin Sweeney, Fort Myers, FL (US); Harlan L. Miller, III, Fort Myers, FL (US)

(73) Assignee: Algenol Biofuels Switzerland GmbH, Zug (CH)

( * ) Notice: Subject to any disclaimer, the term of this patent is extended or adjusted under 35 U.S.C. 154(b) by 0 days.

(21) Appl. No.: 14/472,126

(22) Filed: Aug. 28, 2014

(65) Prior Publication Data

US 2016/0060586 A1 Mar. 3, 2016

(51) Int. Cl.
 *C12M 1/00* (2006.01)
 *C12N 1/20* (2006.01)
 *C12M 3/00* (2006.01)

(52) U.S. Cl.
 CPC ........... *C12M 21/02* (2013.01); *C12M 23/14* (2013.01); *C12M 23/34* (2013.01); *C12M 23/48* (2013.01); *C12M 29/08* (2013.01); *C12N 1/20* (2013.01)

(58) Field of Classification Search
 CPC .................................................. C12M 21/02
 See application file for complete search history.

(56) References Cited

U.S. PATENT DOCUMENTS

| 5,534,417 | A | 7/1996 | Arad et al. |
|---|---|---|---|
| 8,304,209 | B2 | 11/2012 | Van Walsem et al. |
| 2007/0289206 | A1* | 12/2007 | Kertz ............... A01G 15/00 47/1.4 |
| 2008/0160591 | A1 | 7/2008 | Willson et al. |
| 2009/0297073 | A1 | 12/2009 | Sondaar |
| 2010/0028976 | A1* | 2/2010 | Hu ................... C12M 21/02 435/257.1 |
| 2010/0032851 | A1* | 2/2010 | Frankel ............. B01D 69/12 261/122.1 |
| 2010/0285575 | A1 | 11/2010 | Michiels |

(Continued)

FOREIGN PATENT DOCUMENTS

| CA | 2292305 | 6/2000 |
|---|---|---|
| WO | WO2005121309 | 12/2005 |

(Continued)

OTHER PUBLICATIONS

Christenson, et al., "Production and harvesting of microalgae for wastewater treatment, biofuels, and bioproducts", Biotechnology Advances 29, 2011, 686-702.

(Continued)

*Primary Examiner* — Jonathan M Hurst
(74) *Attorney, Agent, or Firm* — David J. Lorenz; Suzanne G. Jepson

(57) ABSTRACT

Photobioreactors having a vertically-oriented enclosure with a thin panel shape, systems, and methods for using the same to culture productive organisms to accumulate biomass and/or make biofuels or other chemical products.

15 Claims, 28 Drawing Sheets

(56) References Cited

U.S. PATENT DOCUMENTS

| | | | | |
|---|---|---|---|---|
| 2011/0124087 A1* | 5/2011 | Meiser | ................... | C12M 21/02 |
| | | | | 435/243 |
| 2011/0151507 A1 | 6/2011 | Van Walsem et al. | | |
| 2011/0306121 A1* | 12/2011 | Chou | ....................... | C12R 1/89 |
| | | | | 435/292.1 |
| 2012/0301563 A1* | 11/2012 | Aikens | ................... | C12M 21/02 |
| | | | | 424/780 |
| 2014/0186909 A1 | 7/2014 | Calzia et al. | | |

FOREIGN PATENT DOCUMENTS

| | | |
|---|---|---|
| WO | WO2007098150 | 8/2007 |
| WO | WO2009040383 | 4/2009 |
| WO | WO2010068288 | 6/2010 |
| WO | WO2013133481 | 9/2013 |

OTHER PUBLICATIONS

PCT/US16/68153, International Search Report and Written Opinion dated Mar. 17, 2017, 11 pages.

* cited by examiner

PHOTOBIOREACTOR, SYSTEM AND METHOD OF USE

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable.

BACKGROUND

The possibility of using algae for the production of fuel and chemicals has attracted the interest of researchers, government and business for many years. Efforts to commercialize the production of fuel from algae using closed photobioreactors have brought to light problems that must be solved to improve the performance of photobioreactors and make the production of biofuels practical.

Various approaches to photobioreactors are the subject of, for example, U.S. Pat. App. Pub. No. 2011/0151507; U.S. Pat. No. 8,304,209; WO/2005/121309; WO/2010/068288; U.S. Pat. No. 5,534,417; WO/2007/098150; WO/2013/133481; U.S. Pat. App. Pub. No. 2008/0160591; U.S. Pat. App. Pub. No. 2010/0285575; WO/2009/040383; and Christenson et al., "Production and harvesting of microalgae for wastewater treatment, biofuels, and bioproducts" *Biotechnology Advances* 29 (2011) 686-702.

An ongoing need exists for photobioreactors, systems and methods that provide, for example, increased volumetric product yields.

SUMMARY

An object of the present invention is a photobioreactor that supports environmental conditions in which productive organisms in a liquid culture inside the enclosure accumulate biomass and/or make biofuels or other chemical products of interest through photosynthesis. A photobioreactor of the present invention may comprise a panel-shaped enclosure with a height that is oriented substantially vertically and further comprises structural features such as point seams that advantageously enhance structural integrity of the enclosure and maintain uniform thickness of the enclosure while minimally impeding flow and mixing of fluids within the enclosure, as well as structural features such as sloped top and bottom edges that facilitate filling and draining of the enclosure. According to the present invention, as the thickness of the enclosure becomes more uniform, the ratio of illuminated liquid culture surface area to liquid culture volume increases, which increases volumetric productivity and product concentration in the liquid culture, thereby reducing energy costs to refine the product. Further according to the present invention, structural features such as sloped top and bottom edges improve operational capabilities of the photobioreactor system.

An aspect of the present invention is directed to a photobioreactor that comprises an enclosure capable of housing a liquid culture of productive organisms and a gas headspace above the liquid culture, wherein the enclosure comprises top, bottom and side edges, a height oriented substantially vertically, a length, a thickness less than either of the height or the length, and a flexible film, at least one portion of the flexible film being translucent; at least one point seam formed in the enclosure; a gas diffuser disposed in a lower portion of the enclosure below the at least one point seam and capable of introducing gas into the enclosure; and a plurality of ports formed in the enclosure.

An additional aspect of the present invention is directed to an enclosure that further comprises a first plurality of point seams spaced apart vertically and horizontally in a first region of the enclosure and a second plurality of point seams spaced apart vertically and horizontally in a second region of the enclosure, wherein vertical spacing among the first plurality of point seams is from about 0.5 inches to about 6 inches, horizontal spacing among the first plurality of point seams is from about 0.5 inches to about 6 inches, vertical spacing among the second plurality of point seams is from about 0.5 inches to about 6 inches, and horizontal spacing among the second plurality of point seams is from about 0.5 inches to about 6 inches.

An additional aspect of the present invention is directed to an enclosure wherein vertical spacing among the first plurality of point seams varies from vertical spacing among the second plurality of point seams.

An additional aspect of the present invention is directed to an enclosure wherein horizontal spacing among the first plurality of point seams varies from horizontal spacing among the second plurality of point seams.

An additional aspect of the present invention is directed to an enclosure further comprising a plurality of point seams in a pattern selected from the patterns shown in FIG. 3 and FIG. 7 and has a length of from about 110 to about 120 inches, a height of from about 50 to about 60 inches, and an average thickness of from about 1.5 to about 2.5 centimeters, further wherein the plurality of point seams have diameters or widths of about 0.75 inches or less, further wherein the pattern shown in FIG. 7 comprises a downcomer channel.

An additional aspect of the present invention is directed to photobioreactor wherein the gas diffuser comprises a tubular shape comprising ethylene propylene diene monomer, the gas diffuser further comprising a length at least about 5 inches less than the length of the enclosure, an inner diameter of from about 0.1 to about 0.25 inches, and a pattern of perforations corresponding to FIG. 6.

An additional aspect of the present invention is directed to photobioreactor further comprising a reinforcement attached to the top edge of the enclosure, the reinforcement comprising rigid polyethylene having a width of about 0.5 inches, a thickness of from about 0.01 to about 0.02 inches, and a length of up to about the length of the enclosure.

A further object of the present invention is a photobioreactor system.

An additional aspect of the present invention is directed to a photobioreactor system further comprising a first header, a second header, a third header and a fourth header in fluid communication with the enclosure through the plurality of ports, wherein the enclosure is filled with the liquid culture from the bottom edge of the enclosure to a fill height and the first header and the second header are positioned above the fill height, the third header is positioned below the fill height and above the bottom edge of the enclosure, and the fourth header is positioned below the bottom edge of the enclosure.

An additional aspect of the present invention is directed to a photobioreactor system wherein ports for liquid addition and gas venting are formed in the top edge of the enclosure near a side edge of the enclosure.

An additional aspect of the present invention is directed to a photobioreactor system further comprising a support structure comprising vertical and horizontal supports, wherein the photobioreactor and the first header, second header, third header and fourth header are suspended from the support structure.

A further object of the present invention is a photobioreactor comprising an enclosure comprising flexible film and capable of housing a liquid culture of productive organisms and a gas headspace above the liquid culture, wherein the enclosure has a height oriented substantially vertically, a length, and a thickness less than either of the height or the length, is adapted to admit light, and is configured to provide a substantially vertically-oriented surface in the plane defined by the length and the width; a gas diffuser disposed in a lower portion of the enclosure and adapted to sparge gas bubbles into the liquid culture in the enclosure; a plurality of point seams formed in the enclosure, wherein the point seams are configured to maintain substantially uniform thickness of the enclosure; and orifices capable of permitting flows of gas and liquid into and out of the enclosure.

A further object of the present invention is a method of culturing productive organisms in a photobioreactor of the present invention comprising the steps of inoculating a photobioreactor with a liquid culture of productive organisms, the photobioreactor comprising an enclosure capable of housing a liquid culture of productive organisms and a gas headspace above the liquid culture, wherein the enclosure comprises a height oriented substantially vertically, a length, a thickness less than either of the height or the length, and a flexible film, at least one portion of the flexible film being translucent; at least one point seam formed in the enclosure; a gas diffuser disposed in a lower portion of the enclosure below the at least one point seam and capable of introducing gas into the enclosure; and a plurality of ports formed in the enclosure; exposing the liquid culture of productive organisms to photosynthetically active radiation; adding carbon dioxide to the enclosure through the gas diffuser; and removing oxygen from the enclosure through at least one of the plurality of ports.

An additional aspect of the present invention is a method of culturing productive organisms in a photobioreactor wherein the enclosure further comprises a first plurality of point seams spaced apart vertically and horizontally in a first region of the enclosure and a second plurality of point seams spaced apart vertically and horizontally in a second region of the enclosure, wherein vertical spacing among the first plurality of point seams is from about 0.5 inches to about 6 inches, horizontal spacing among the first plurality of point seams is from about 0.5 inches to about 6 inches, vertical spacing among the second plurality of point seams is from about 0.5 inches to about 6 inches, and horizontal spacing among the second plurality of point seams is from about 0.5 inches to about 6 inches.

An additional aspect of the present invention is a method of culturing productive organisms in a photobioreactor wherein vertical spacing among the first plurality of point seams varies from vertical spacing among the second plurality of point seams.

An additional aspect of the present invention is a method of culturing productive organisms in a photobioreactor wherein horizontal spacing among the first plurality of point seams varies from horizontal spacing among the second plurality of point seams.

An additional aspect of the present invention is a method of culturing productive organisms in a photobioreactor wherein the enclosure further comprises a plurality of point seams in a pattern selected from the patterns shown in FIG. 3 and FIG. 7 and has a length of from about 110 to about 120 inches, a height of from about 50 to about 60 inches, and an average thickness of from about 1.5 to about 2.5 centimeters, further wherein the plurality of point seams have diameters or widths of about 0.75 inches or less, further wherein the pattern shown in FIG. 7 comprises a downcomer channel.

An additional aspect of the present invention is a method of culturing productive organisms in a photobioreactor wherein the gas diffuser comprises a tubular shape comprising ethylene propylene diene monomer, the gas diffuser further comprising a length at least about 5 inches less than the length of the enclosure, an inner diameter of from about 0.1 to about 0.25 inches, and a pattern of perforations corresponding to FIG. 6.

An additional aspect of the present invention is a method of culturing productive organisms in a photobioreactor further comprising controlling concentration of carbon dioxide in the gas headspace to a preselected value through the addition of carbon dioxide to the enclosure; and controlling gas pressure inside the enclosure within a range from about 2 to about 6 inches of water by venting or adding gas through at least one of the plurality of ports.

An additional aspect of the present invention is a method of culturing productive organisms in a photobioreactor wherein the liquid culture of productive organisms produces biomass, further comprising removing the biomass from the enclosure.

An additional aspect of the present invention is a method of culturing productive organisms in a photobioreactor wherein the liquid culture of productive organisms produces a biofuel, further comprising removing the biofuel from the enclosure.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE SEVERAL VIEWS OF THE DRAWING

Embodiments of the invention will be described below with reference to the following figures.

DETAILED DESCRIPTION

Figure 1:
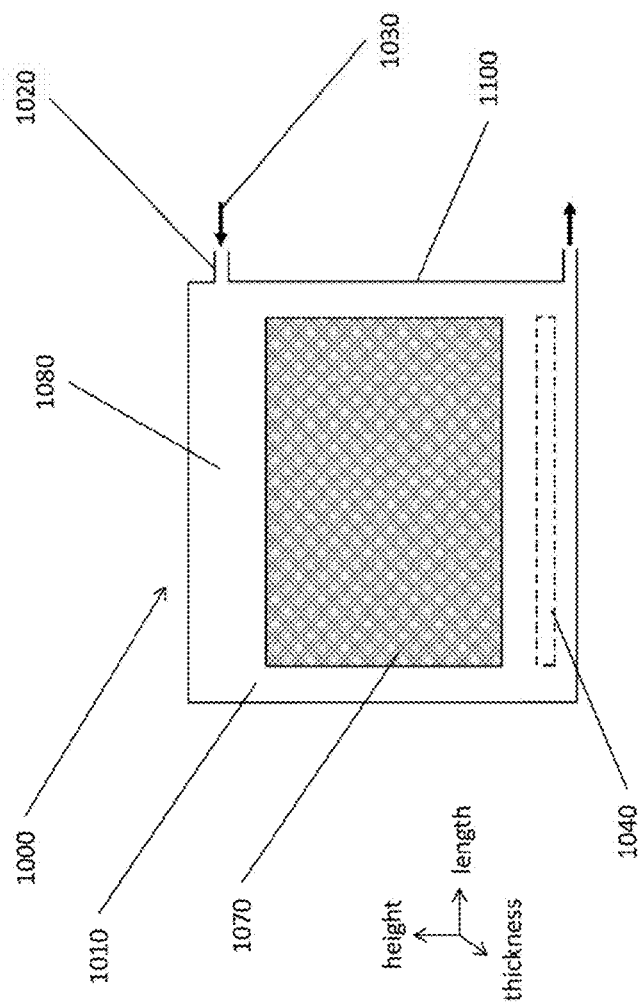
FIG. 1 shows a plan view of a general structure of a photobioreactor design.

The present invention relates to photobioreactors, systems and methods for using a wild-type or metabolically enhanced microorganism in a photobioreactor of the present invention to develop biomass or make chemical products, in particular biofuels such as ethanol, through photosynthesis.

As used herein, the term "productive organism" means a microorganism that carries out photosynthesis and accumulates biomass in wild-type form, and also is competent to be metabolically enhanced, such that the enhanced microorganism metabolizes an intermediate that is made through photosynthesis and converts the intermediate into a chemical product of interest. The cell can be a prokaryotic or a eukaryotic cell. The term is intended to include progeny of the cell originally metabolically enhanced. Non-limiting examples of productive organisms within the meaning of the present invention are *Cyanobacterium, Synechococcus, Synechocystis* and *Chlorogloeopsis* species. In some embodiments, the cell is a prokaryotic cell, e.g., a cyanobacterial cell. One of ordinary skill in the art will recognize that other productive organisms are within the scope of the present invention.

For commercial-scale operations employing a photobioreactor system of the present invention, it is preferable to use a productive organism that is metabolically enhanced in a manner such that the productive organism produces only, or predominantly, one target product. Metabolic enhancements that are effective to achieve this result may be implemented by using known genetic engineering techniques to introduce selected genes into cells of the productive organism. Examples of metabolically enhanced microorganisms that produce ethanol through conducting photosynthesis are disclosed in U.S. Pat. No. 6,306,639 to Woods et al. titled "Genetically Modified Cyanobacteria For The Production Of Ethanol, The Constructs And Method Thereof."

As used herein, the term "photosynthesis" means a process used by organisms to convert light energy captured from the sun into chemical energy that can be used to fuel the organism's activities. In productive organisms of the present invention, light energy and carbon are further converted into chemical products such as biofuels.

As used herein, the term "chemical product" means an organic compound made by a productive organism through photosynthesis. Non-limiting examples of chemical products are biofuels.

As used herein, the term "biofuel" means a type of fuel that derives energy from biological carbon fixation. Biofuels include fuels derived from biomass conversion or from cell metabolism, as well as solid biomass, liquid fuels and various biogases. Biofuels may be produced by the action of enhanced productive organisms through photosynthesis. A non-limiting example of a biofuel is ethanol.

As used herein, the term "photobioreactor" means a device or system used to support a biologically active environment for the cultivation of productive organisms in water or a liquid medium that contains nutrients and other growth-promoting constituents. A photobioreactor of the present invention may be constructed of translucent materials that permit penetration of light, or may otherwise incorporate a light source to provide photonic energy input for an aqueous culture of photosynthetic microorganisms contained therein. A photobioreactor of the present invention may be closed or semi-closed against the exchange of gases and contaminants with the outside environment. A photobioreactor of the present invention may be constructed from a flexible film or from a rigid thermoplastic.

As used herein, the term "translucent" means allowing light to pass through, with or without scattering of photons.

As used herein, the term "flexible film" means a continuous polymeric material or coating that is not structurally self-supporting, and preferably is at least partially translucent. Non-limiting examples of materials that can be used in flexible films suitable for use with the present invention are polyolefins, polyesters and vinyl copolymers thereof, including polyethylene, polypropylene, nylon, ethylene vinyl acetate and polyvinyl chloride.

As used herein, the term "point seam" means discrete portions of flexible film bonded together through radio frequency welding, ultrasonic welding, impulse welding, thermoforming or any other suitable technique, the discrete bonded film portions having the shape of, for example, a circle, oval, polygon with rounded corners or irregular form with rounded corners.

As used herein, the term "thermoplastic" means a continuous polymeric material or coating that is rigid and substantially structurally self-supporting, and preferably is at least partially translucent. Non-limiting examples of thermoplastics suitable for use with the present invention are polycarbonate and polymethyl methacrylate.

As used herein, the term "header" means a chamber, such as a length of pipe, to which the ends of a number of conduits, such as tubes or pipes typically of smaller diameter than the header, are connected so that liquids and/or gases are distributed from the header among the conduits (supply) or are collected in the header from the conduits (exhaust).

As used herein, the term "sparging" means a process whereby a gas is bubbled through a fluid.

As used herein, the term "gas diffuser" means a mechanical device that sparges a gas to control its velocity and enhance its mixing into a surrounding fluid.

As used herein, the term "proportional-integral-derivative controller" or "PID controller" means a control loop feedback mechanism (controller) that calculates an error value as the difference between a measured process variable and a desired setpoint, and attempts to minimize the error by adjusting the process through use of a manipulated variable.

As used herein, the term "medium" means a liquid or gel designed to support the growth of microorganisms.

As used herein, the terms "optical density" or "OD" mean a measure of light scattered by a suspension of microorganisms, which manifests as absorbance. Increasing optical density indicates increasing biomass or cell abundance.

As used herein, the term "$OD_{750}$" means scattering of light having a wavelength of 750 nm. Measurements of $OD_{750}$ for the same sample can vary when measured by different spectrophotometers, necessitating a standardization protocol.

As used herein, the term "in fluid communication with" means a connection that permits the passage of liquids or gases between the recited components.

As used herein, the term "metabolically enhanced" means any change in the endogenous genome of a productive organism or to the addition of non-endogenous genetic code to a productive organism, e.g., the introduction of a heterologous gene. More specifically, such changes are made by the hand of man through the use of recombinant DNA technology or mutagenesis. The changes can involve protein coding sequences or non-protein coding sequences.

As used herein, the term "about" means approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) within a confidence interval of 90% or 95%.

FIG. 1 shows a generic embodiment of a photobioreactor system 1000 of the present invention that comprises a photobioreactor enclosure 1010. In some embodiments, the photobioreactor enclosure 1010 is capable of housing a liquid culture of productive organisms 1070 that fills the photobioreactor enclosure 1010 partially or fully, and a headspace 1080 filled with gas above the surface of the liquid in any portion of the photobioreactor enclosure 1010 that is not filled with liquid.

The shape and dimensions of the photobioreactor enclosure 1010 may be selected to maximize the ratio of surface area to volume, in order to maximize light exposure and distribution over productive organisms 1070 within the liquid culture. In some embodiments, the shape of the photobioreactor enclosure 1010 is a thin panel.

The photobioreactor enclosure 1010 may be configured to accommodate entering and exiting flows 1030 of gas and liquid through openings or ports 1020 in the photobioreactor enclosure 1010.

The photobioreactor system 1000 may comprise a gas diffuser 1040 that is configured to introduce gas flows 1030 through a port 1020 into the contents of the photobioreactor enclosure 1010.

The photobioreactor enclosure 1010 may comprise flexible film that forms two opposing walls 1060. The opposing walls 1060 may be formed by, for example, two separate sheets of flexible film, one folded sheet of flexible film, or a tube or cylinder of flexible film.

Figure 2:
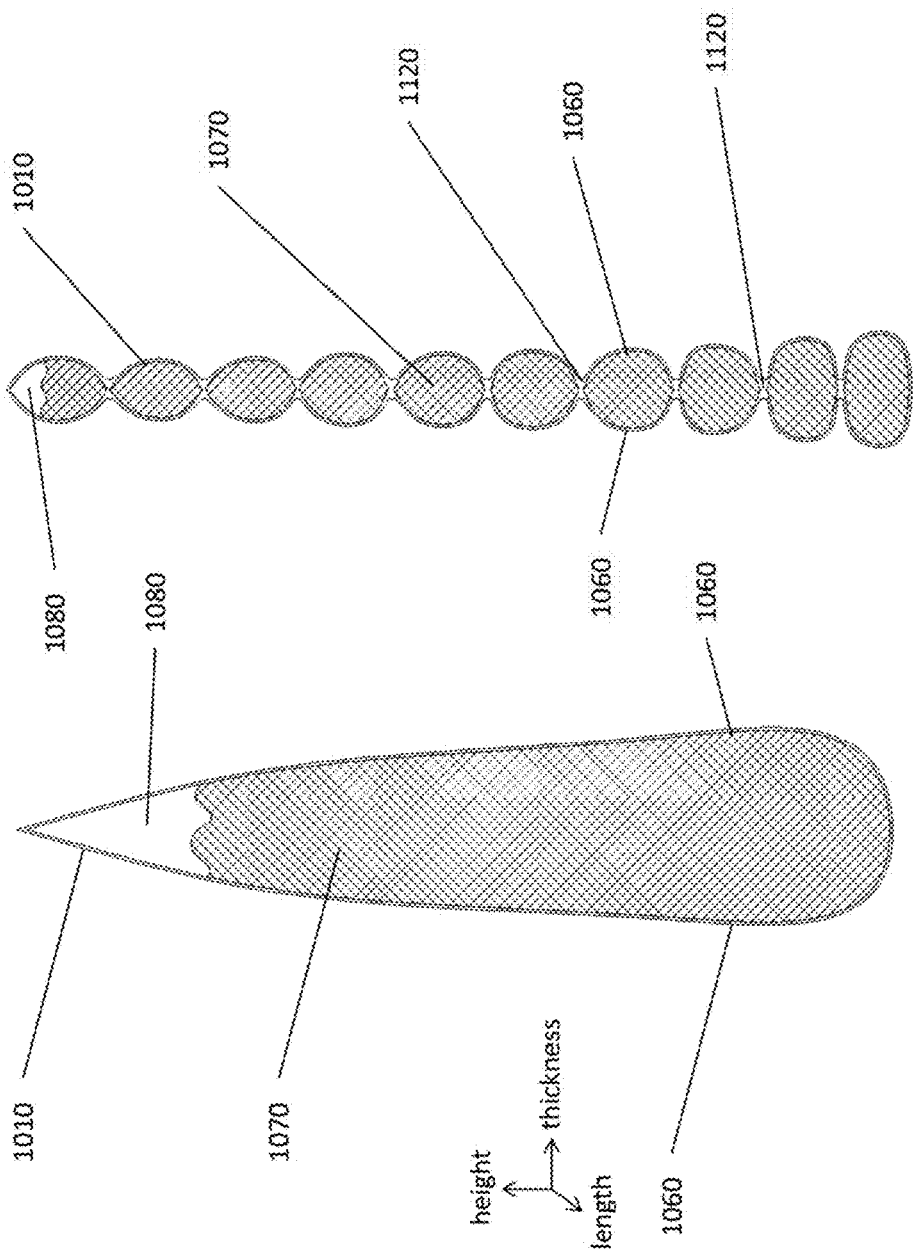
FIG. 2A shows a sectional view of a photobioreactor design.
FIG. 2B shows a sectional view of a photobioreactor design of the present invention.

As shown in FIGS. 2A and 2B, liquids and/or gases contained in the photobioreactor enclosure 1010 exert outward pressure that tends to induce curvature of the opposing walls 1060. The photobioreactor enclosure 1010 may further comprise structural features configured to enhance structural integrity and maintain substantially planar and parallel opposing walls 1060.

In some embodiments, opposing walls 1060 comprising flexible film are bonded together through radio frequency welding, ultrasonic welding, impulse welding, thermoforming or any other suitable technique to create bonded seams at the perimeter 1100 of the photobioreactor enclosure 1010. Exemplary properties of a suitable flexible film for use in a photobioreactor enclosure 1010 of the present invention are translucency, tolerance to UV radiation, low cost, light weight and acceptable durability.

In some embodiments, at least one opposing wall 1060 of the photobioreactor enclosure 1010 is translucent or transparent for the purpose of allowing exposure of productive organisms 1070 in the internal void volume to light from the sun or another source that provides photosynthetically active radiation having wavelengths from 400 to 700 nanometers. The productive organisms 1070 utilize the light to accumulate biomass and/or make chemical products of interest, such as biofuels, through photosynthesis.

The dimensions of the photobioreactor enclosure 1010 can be selected to optimize properties such as photosynthetic efficiency of productive organisms 1070 contained in the photobioreactor enclosure 1010 and productivity per unit cost of capital and operation, as determined by considerations of light exposure and dilution, dynamics of mixing of liquids and gases in the photobioreactor enclosure 1010 and costs of build materials, energy inputs and supporting structures, for example. In some embodiments, the height of the photobioreactor enclosure 1010 ranges from about 2 feet to about 5 feet, and more preferably from about 2.5 feet to about 3.5 feet. In some embodiments, the length of the photobioreactor enclosure 1010 ranges from about 3 feet to about 30 feet, and more preferably from about 9 feet to about 15 feet. In some embodiments, the maximum cross-sectional average thickness of the photobioreactor enclosure 1010 ranges from about 1 centimeter to about 3 centimeters, more preferably from about 1.0 centimeters to about 2 centimeters. The orientation of the height of the photobioreactor enclosure 1010 is substantially vertical, and the orientation of the length and thickness of the photobioreactor enclosure 1010 are substantially horizontal and orthogonal.

Figure 3:
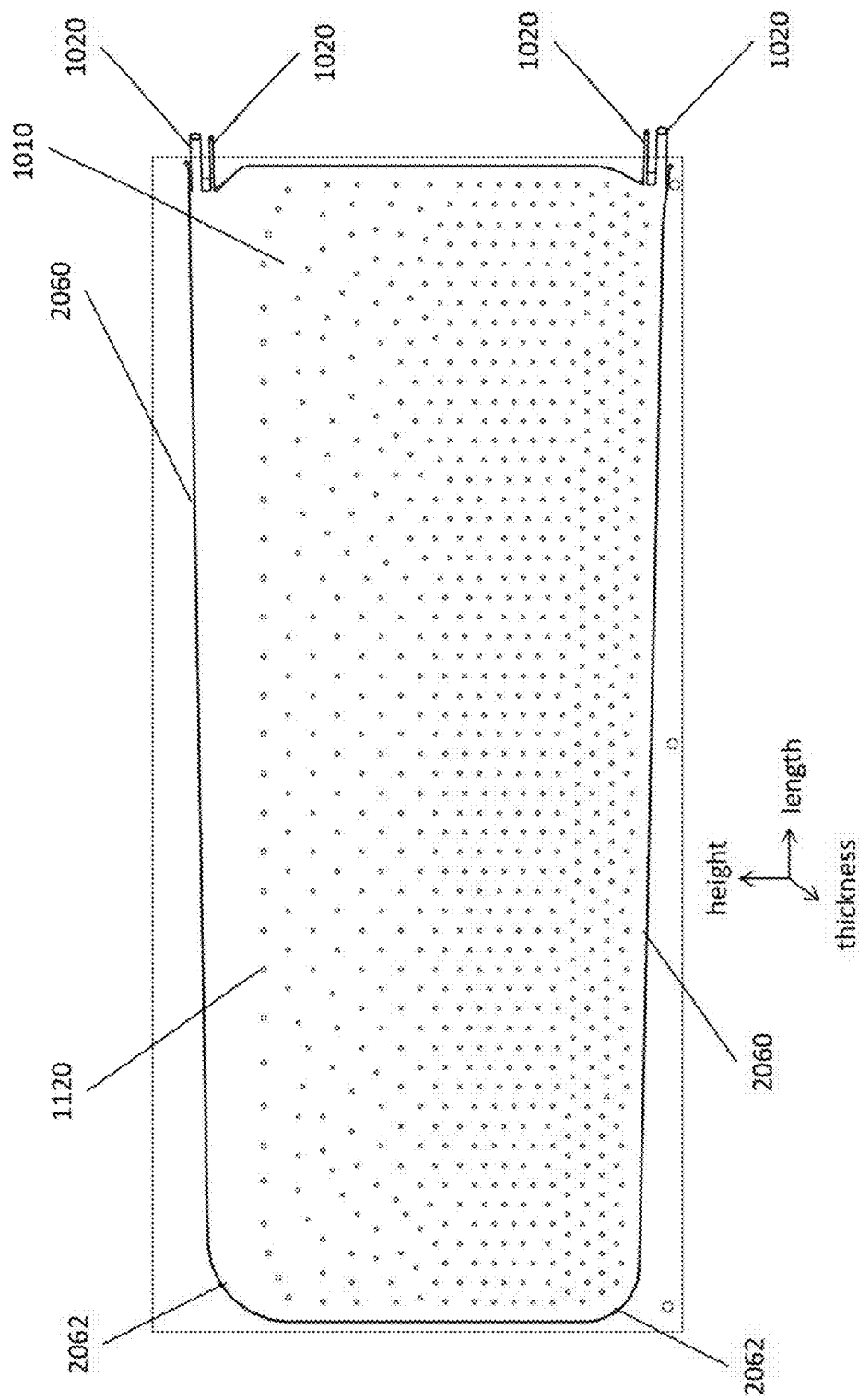
FIG. 3 shows a plan view of a photobioreactor design of the present invention.

FIG. 3 shows an embodiment of a photobioreactor system 1000 configured as a thin panel photobioreactor enclosure 1010 with an internal void volume. In some embodiments, the height of the photobioreactor enclosure 1010 is oriented more or less vertically. In some embodiments, the photobioreactor enclosure 1010 is constructed of flexible film and comprises point seams 1120 dispersed within the void volume of the photobioreactor enclosure 1010. The point seams 1120 may be formed by, for example, bonding together discrete portions of the opposing walls 1060 comprising the flexible film so as to create bonded seams. The diameter or width of the point seams 1120 is in the plane defined by the length and width of the photobioreactor enclosure 1010.

In some embodiments, point seams 1120 enhance structural integrity of the photobioreactor enclosure 1010 by dispersing fluid pressure exerted on the opposing walls 1060, and also minimally impede flow and mixing of liquids and gases in the photobioreactor enclosure 1010.

Pressure head from liquid completely or partially filling a photobioreactor enclosure 1010 constructed of flexible film tends to displace the opposing walls 1060 apart. In a photobioreactor enclosure 1010 without point seams 1120, as shown in FIG. 2A, the pressure head creates a bulge at or near the bottom of the photobioreactor enclosure 1010, such that the thickness of a lower portion of the photobioreactor enclosure 1010 is greater than the thickness of an upper portion of the photobioreactor enclosure 1010. In a photobioreactor enclosure 1010 comprising point seams 1120, as shown in FIG. 2B, the point seams 1120 increase the surface area and points of attachment between the opposing walls 1060 and constrain the displacement of the opposing walls 1060, thereby reducing bulging. In some embodiments, the thickness of a flexible film photobioreactor enclosure 1010 comprising point seams 1120 and completely or partially filled with liquid is substantially more uniform than the thickness of a flexible film photobioreactor enclosure 1010 without point seams 1120, as shown in FIGS. 2A and 2B.

According to the present invention, as the thickness of a photobioreactor enclosure 1010 containing a liquid culture of productive organisms 1070 becomes more uniform and bulging diminishes, the ratio of illuminated liquid culture surface area to liquid culture volume increases. Consequently, volumetric productivity of the liquid culture of productive organisms 1070 increases, which increases product concentration in the liquid culture and advantageously reduces costs to refine product made by the liquid culture. In some embodiments of a photobioreactor enclosure 1010 containing a static volume of liquid culture, the ratio of illuminated liquid culture surface area to liquid culture volume and the volumetric productivity are higher with point seams 1120 disposed in the photobioreactor enclosure 1010, as in FIG. 2B, than without point seams 1120, as in FIG. 2A.

Under pressure head from liquid filling a photobioreactor enclosure 1010, opposing walls 1060 comprising flexible film may fold or crease between point seams 1120 and contact each other, thereby restricting fluid flow in the photobioreactor enclosure 1010. In some embodiments, the photobioreactor enclosure 1010 comprises point seams 1120 that are spaced apart so as to distribute mechanical stresses in a manner that minimizes or substantially eliminates formation of folds or creases in the walls 1060.

In some embodiments, point seam 1120 diameter or width is about 0.75 inches or smaller. In some embodiments, point seam 1120 diameter or width is from about 0.375 to about 0.75 inches. In some embodiments, the shape of the point seam 1120 is a circle, oval, polygon with rounded corners or irregular form with rounded corners. According to the present invention, rounded or large-angle corners in the point seam 1120 shape are beneficial to fabrication of the point seam 1120 and resistance of the point seam 1120 to tearing and creating a leak in the photobioreactor enclosure 1010. In some embodiments, a point seam 1120 has any discrete shape and size that are suitable to enhance structural integrity of the photobioreactor enclosure 1010 while minimally impeding fluid flow and mixing therein.

Mechanical stress incident on a first point seam 1120 located in a first region of a photobioreactor enclosure 1010 may differ substantially from mechanical stress incident on a second point seam 1120 located in a distinct second region of the photobioreactor enclosure 1010, due to differences in, for example, pressure head and mass of the photobioreactor enclosure 1010 below the point seam 1120. In some embodiments, for the purpose of maintaining uniform thickness of the photobioreactor enclosure 1010, spacing between point seams 1120 in different regions of a photobioreactor enclosure 1010 is varied to compensate for varying mechanical stresses incident on the point seams 1120 in different regions. In some embodiments, vertical or horizontal spacing between point seams 1120 in different regions of a photobioreactor enclosure 1010 varies from about 0.5 inches to about 6 inches.

In some embodiments, a flexible film photobioreactor enclosure 1010 comprises a strip of material bonded to the flexible film along the length of the top edge of the photobioreactor enclosure 1010. The strip of material reinforces the flexible film and resists folding. In some embodiments, the material is rigid polyethylene. In some embodiments, the strip of material is about 0.5 inches wide, from about 0.01 to about 0.02 inches thick, and up to about the length of the photobioreactor enclosure 1010. In some embodiments, multiple strips of the material are bonded to the photobioreactor enclosure 1010.

Photobioreactor enclosures 1010 of the present invention comprise openings, orifices, or ports 1020, to allow, for example, the addition and removal of liquids and gases to and from the internal void volume of the photobioreactor enclosure 1010 and the insertion of probes for monitoring pH, temperature, oxygen concentration, carbon dioxide concentration, ethanol concentration and other properties within the photobioreactor enclosure 1010.

As shown in, for example, FIG. 3, in some embodiments, a port 1020 for liquid addition is positioned near a top edge of the photobioreactor enclosure 1010, a port 1020 for liquid removal is positioned near a bottom edge of the photobioreactor enclosure 1010, a port 1020 for gas addition is positioned near a bottom edge of the photobioreactor enclosure 1010 and a port 1020 for gas venting is positioned near a top edge of the photobioreactor enclosure 1010. In this configuration, liquid can be added to a partially filled photobioreactor enclosure 1010 and the outlet port 1020 for liquid acts as a gravity drain. A gas addition line positioned near or above the top of the photobioreactor enclosure 1010 can be diverted to introduce gas to the bottom of the photobioreactor enclosure 1010, so as to bubble gas upward through liquid contained in the photobioreactor enclosure 1010 with the gas outlet near the top of the photobioreactor enclosure 1010.

In some embodiments, ports 1020 are formed in a side edge of the photobioreactor enclosure 1010 near the top or bottom edge of the photobioreactor enclosure 1010, as shown in, for example, FIG. 3. In some embodiments, ports 1020 are formed in the top or bottom edge of the photobioreactor enclosure 1010 near a side edge of the photobioreactor enclosure 1010. In some embodiments, ports 1020 for liquid addition and gas venting are formed in the top edge of the photobioreactor enclosure 1010 near a side edge of the photobioreactor enclosure 1010.

Ports 1020 for gas and liquid flows 1030 are fitted with valves, pumps, fans and other suitable fitments that enable control over flow rates and ensure that the photobioreactor enclosure 1010 can remain sealed.

Figure 4:
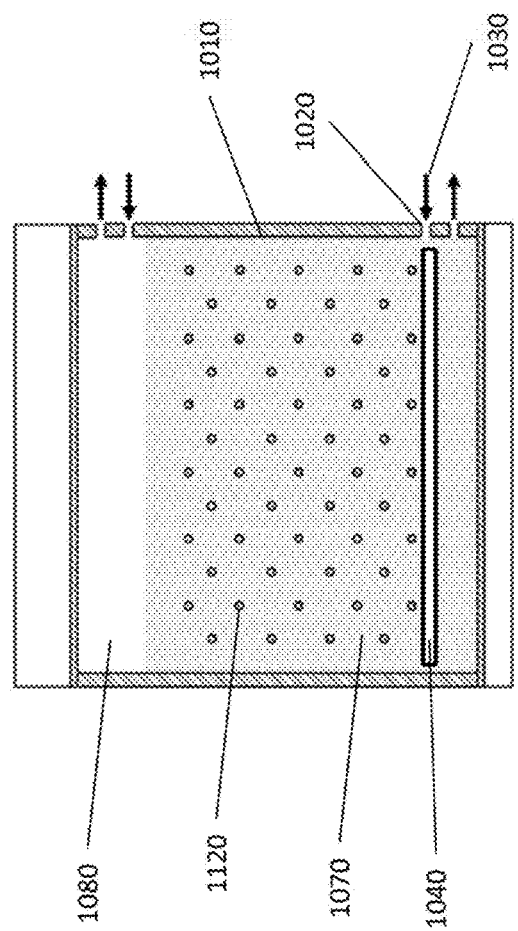
FIG. 4 shows a plan view of a photobioreactor design of the present invention.
Figure 5:
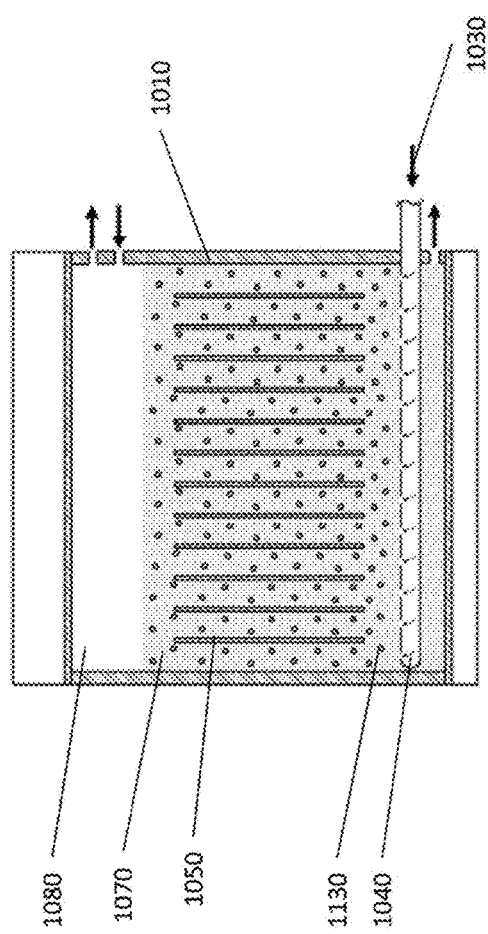
FIG. 5 shows a plan view of a photobioreactor design of the present invention.

As shown in FIGS. 4 and 5, in some embodiments, a gas diffuser 1040 is positioned in the bottom of the photobioreactor enclosure 1010 and connected to an inlet port 1020 for gas flows 1030 positioned near the bottom of the photobioreactor enclosure 1010. In some embodiments, the gas diffuser 1040 is a tube, or sparging hose, that is perforated partially or completely along its length, with roughly circular, oval or similarly-shaped holes. Gas is sparged through liquid culture medium contained in the photobioreactor enclosure 1010 by directing gas flows 1030 through the inlet port 1020 and the gas diffuser 1040. The gas escapes through the perforations in the gas diffuser 1040 and forms bubbles 1130 that rise through the culture medium into the gas headspace 1080, where the gas is expelled though an outlet port 1020.

The gas diffuser 1040 may be made of natural rubber, ethylene propylene diene monomer, nitrile rubber, fluoroelastomer rubber, plastic, foam rubber, dense rubber, silicone rubber or any other material that is suitably impermeable to act as a conduit for gas but can be perforated to enable selective escape of the gas. The gas diffuser 1040 preferably is made of a low cost material that is flexible so as to increase its resistance to fouling and provide more uniform bubble 1130 distributions in comparison to rigid diffusers. The material selected for the gas diffuser 1040 preferably is resistant to exposure to sterilizing agents, and minimizes pressure drop along the length of the gas diffuser 1040, but maintains a minimum pressure drop across the gas diffuser 1040 that is substantially greater than the static pressure head variation to which the gas diffuser 1040 is subject because of its variation in depth. Any materials used in construction of the gas diffuser 1040 should be nontoxic or capable of being detoxified. The gas diffuser 1040 is fashioned such that it provides control over perforation aperture size and bubble 1130 diameter.

Figure 6:
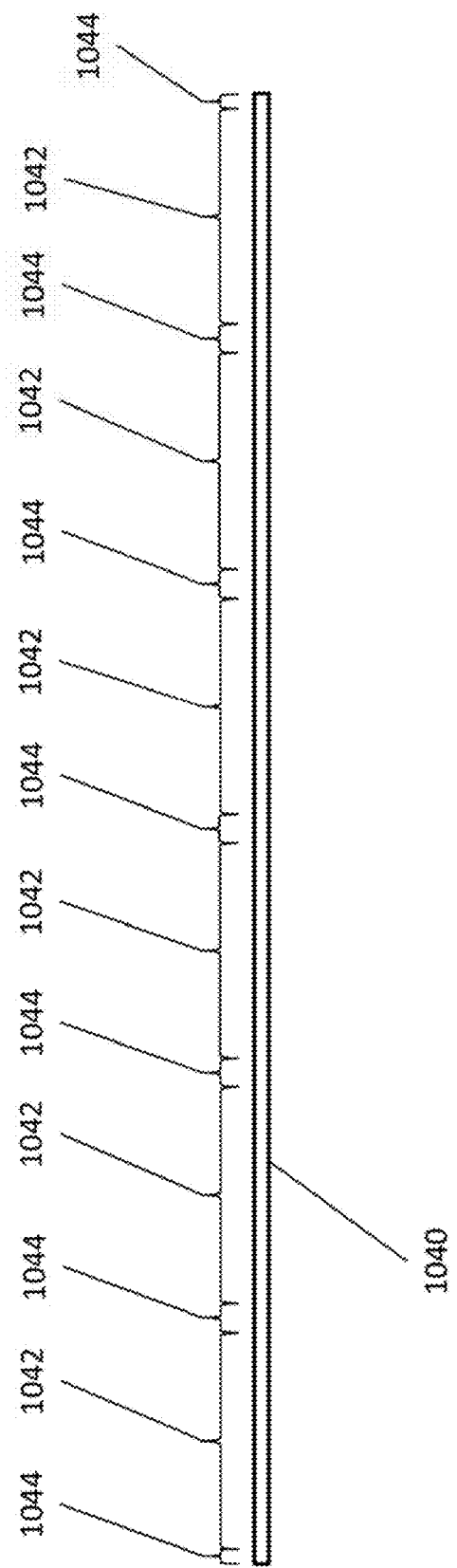
FIG. 6 shows a plan view of a gas diffuser of the present invention.

In some embodiments, as illustrated in FIG. 6, a tubular gas diffuser 1040 is configured with repeating perforated sections 1042 and non-perforated sections 1044. Each non-perforated section 1044 is from about 0 to about 5 inches long, preferably from about 1.5 inches to about 5 inches long. Each perforated 1042 section is from about 15 inches long to about the length of the gas diffuser 1040, with from about 1 to about 6 perforations per inch and perforation diameter of from about 0.03 to about 0.08 inches. Total length of the gas diffuser 1040 is less than or almost as long as the photobioreactor enclosure 1040, in some embodiments from about 105 to about 115 inches, and inner diameter of the gas diffuser 1040 is from about 0.1 to about 0.25 inches to accommodate varying gas pressures and flowrates. In some embodiments, the gas diffuser 1040 comprises ethylene propylene diene monomer.

Gas is sparged into portions of the liquid culture medium above the perforated sections 1042, while gas is not sparged into other portions of the liquid culture medium above the non-perforated sections 1044. According to the present invention, the pattern of alternating sparging and non-sparging induces mixing throughout the liquid culture medium.

Figure 7:
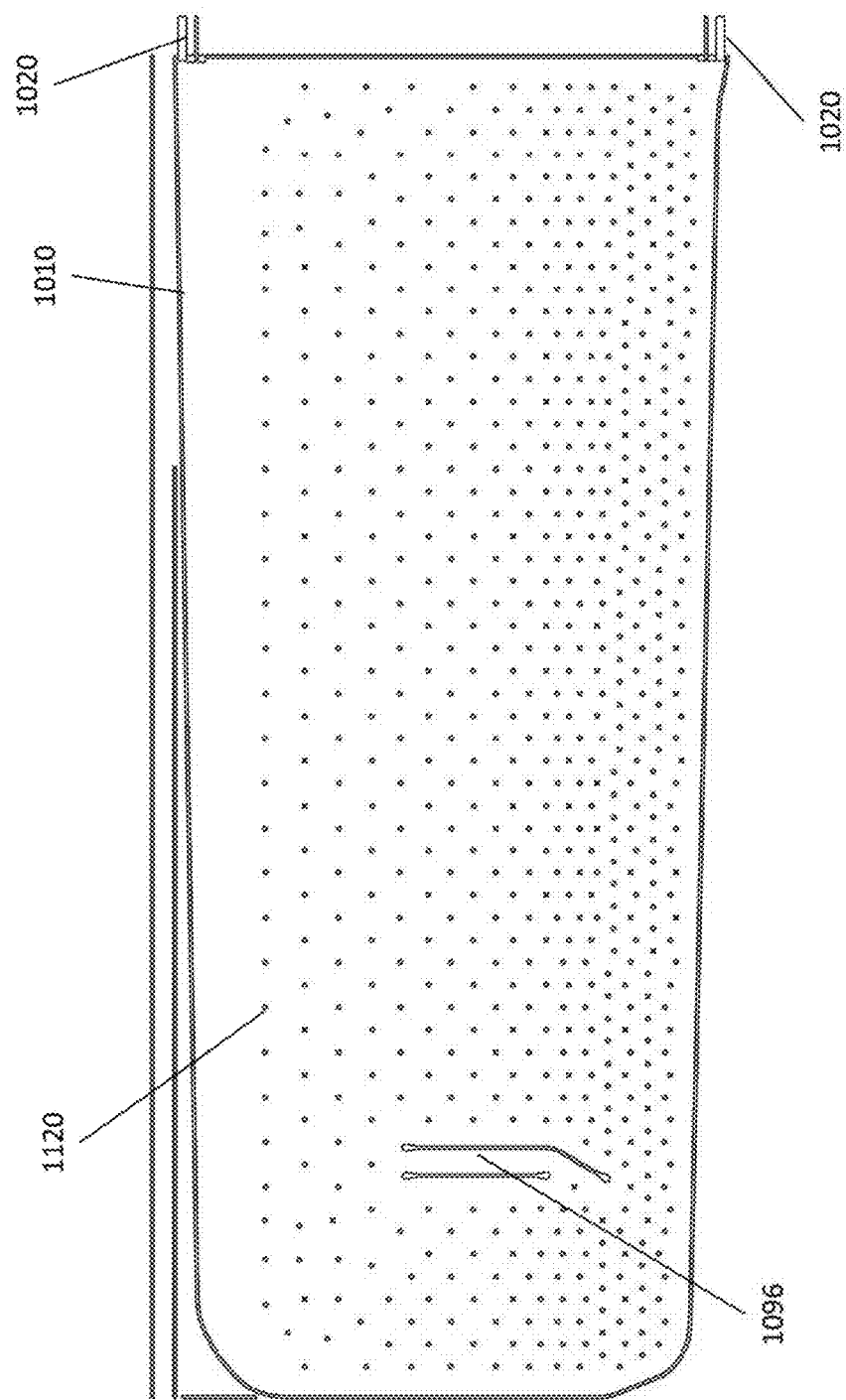
FIG. 7 shows a plan view of a photobioreactor design of the present invention.

In some embodiments, such as shown in FIG. 7, a downcomer channel 1096 formed by bonding together portions of the opposing walls 1060 to create seams is disposed in the central portion of the photobioreactor enclosure 1010 and features an elongated, angled edge at the bottom of the downcomer channel 1096 that deflects gas bubbles 1130 (not shown) introduced by the gas diffuser 1040 (not shown) from entering the downcomer channel 1096. The downcomer channel 1096 is submerged in the liquid culture of productive organisms 1070 (not shown) disposed in the photobioreactor enclosure 1010, such that the downcomer channel 1096 is in fluid communication with the sparged portion of the photobioreactor enclosure 1010. Gas bubbles 1130 (not shown) from the gas diffuser 1040 (not shown) mix liquid culture upward in the portions of the photobioreactor enclosure 1010 adjacent to the downcomer channel 1096, and liquid culture flows downward in the non-sparged downcomer channel 1096. Horizontal mixing of the liquid culture between the downcomer channel 1096 and the portions of the photobioreactor enclosure 1010 adjacent to the downcomer channel 1096 occurs in the portions of the liquid culture that are above the top ends and below the bottom ends of the downcomer channel 1096.

Figure 8:
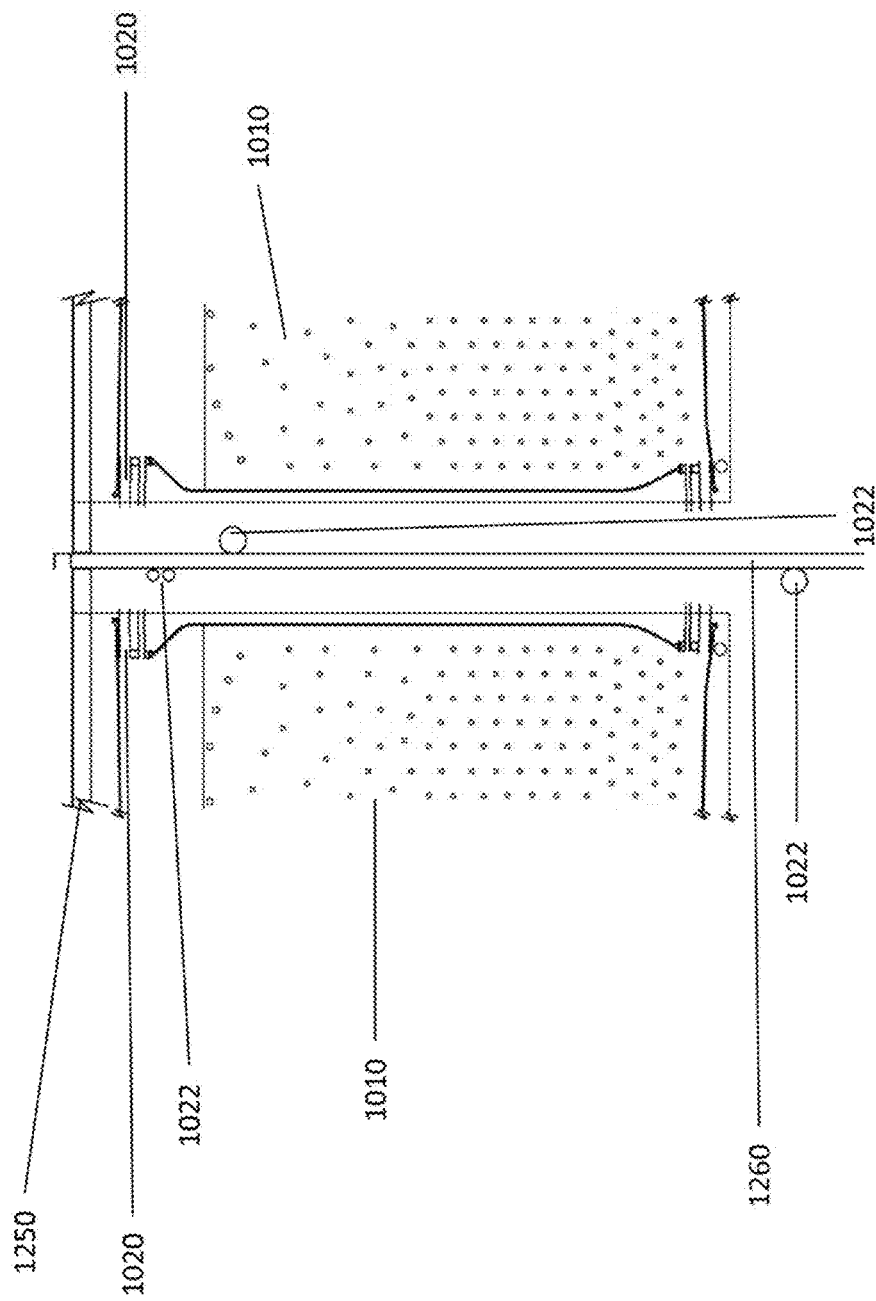
FIG. 8 shows a sectional plan view of a photobioreactor design, portions of a support structure and headers of the present invention.

In some embodiments, such as shown in FIG. 8, a port 1020 is connected by tubing or piping (not shown) to a header 1022 positioned outside of the photobioreactor enclosure 1010, such that multiple photobioreactor enclosures 1010 may each be connected to common headers 1022 for gas flow 1030 into the photobioreactor enclosure 1010, gas flow 1030 out of the photobioreactor enclosure 1010, liquid flow 1030 into the photobioreactor enclosure 1010, and liquid flow 1030 out of the photobioreactor enclosure 1010.

In some embodiments, a header 1022 for liquid flow 1030 out is positioned below the bottoms of the photobioreactor enclosures 1010, so that liquid can be drained by gravity feed from the photobioreactor enclosures 1010 to the header 1022.

In some embodiments, a header 1022 for liquid flow 1030 in is positioned above the tops of the photobioreactor enclosures 1010, or above the height of the liquid filling the photobioreactor enclosures 1010.

In some embodiments, a header 1022 for gas flow 1030 in is positioned above the tops of the photobioreactor enclosures 1010, or above the height of the liquid filling the photobioreactor enclosures 1010, and connected by tubing or piping to a gas diffuser 1040 positioned in the bottom of the photobioreactor enclosure 1010 so that liquid in the photobioreactor enclosure 1010 is prevented from flooding the header, in the event gas flow 1030 through the gas diffuser 1040 is interrupted.

In some embodiments, a header 1022 for gas flow 1030 out is positioned below the height of the liquid filling the photobioreactor enclosures 1010 in order to minimize pressure within the photobioreactor enclosures 1010 in the event that liquid flow 1030 is forced out of the photobioreactor enclosures 1010 through the header 1022 for gas flow 1030 out, as necessitated by operation of the photobioreactor system 1000.

It is desirable to minimize the cost of the photobioreactor system 1000 and associated supporting structures relative to the value of the product made by the productive organisms 1070. One of ordinary skill in the art will appreciate that suitable flexible films may be selected for use in constructing photobioreactor enclosures 1010 of the present invention for the purpose of maximizing economic efficiency. The selection of materials suitable for use in constructing the photobioreactor enclosures 1010 and supporting structures may be influenced by considerations of, for example, the total weight of liquid, gas and productive organisms 1070 contained in the photobioreactor enclosure 1010 or the desired degree of translucency or light scattering for a liquid culture of productive organisms 1070.

Figure 9:
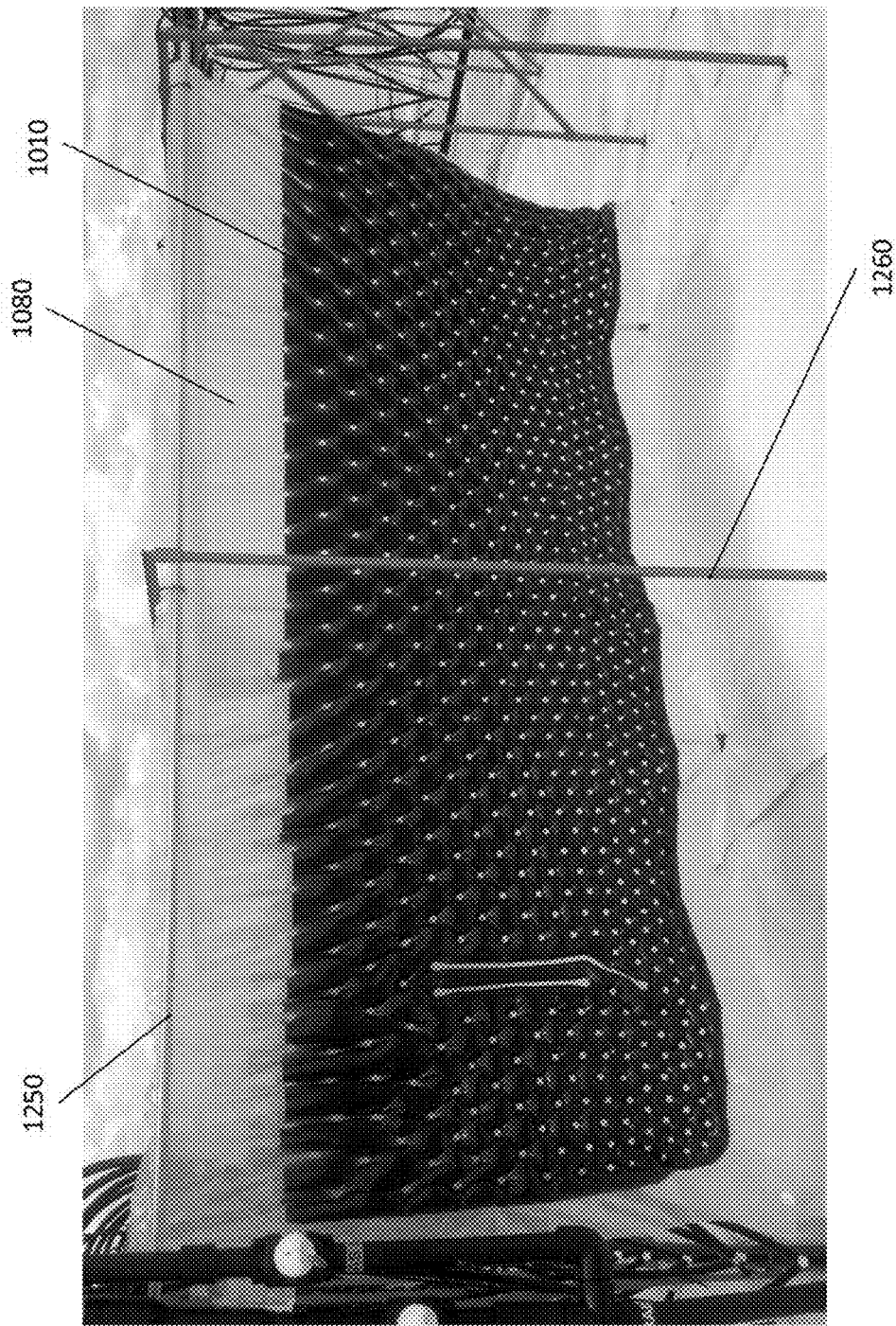
FIG. 9 shows a perspective view of a photobioreactor design and portions of a support structure of the present invention.
Figure 10:
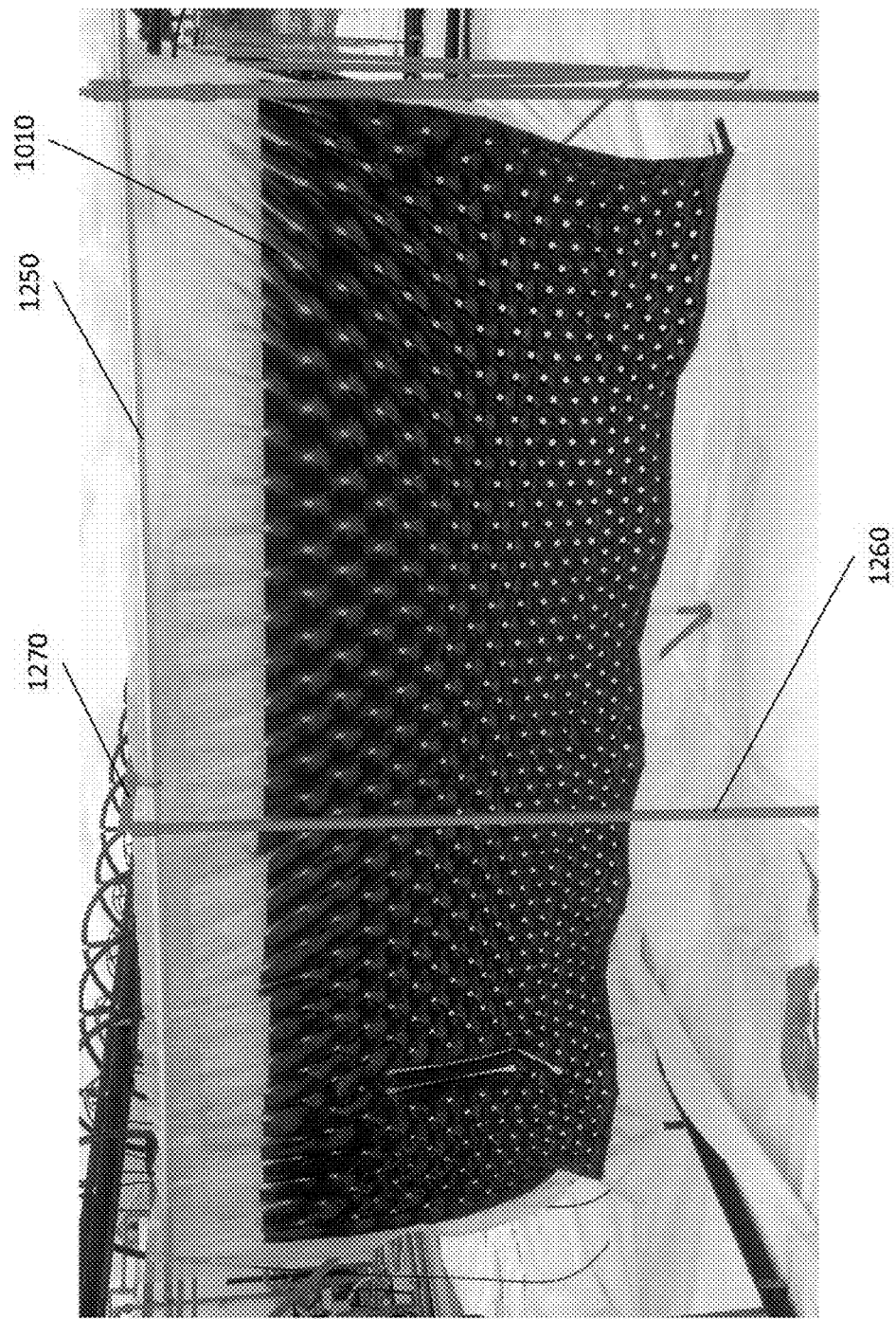
FIG. 10 shows a perspective view of a photobioreactor design and portions of a support structure of the present invention.
Figure 11:
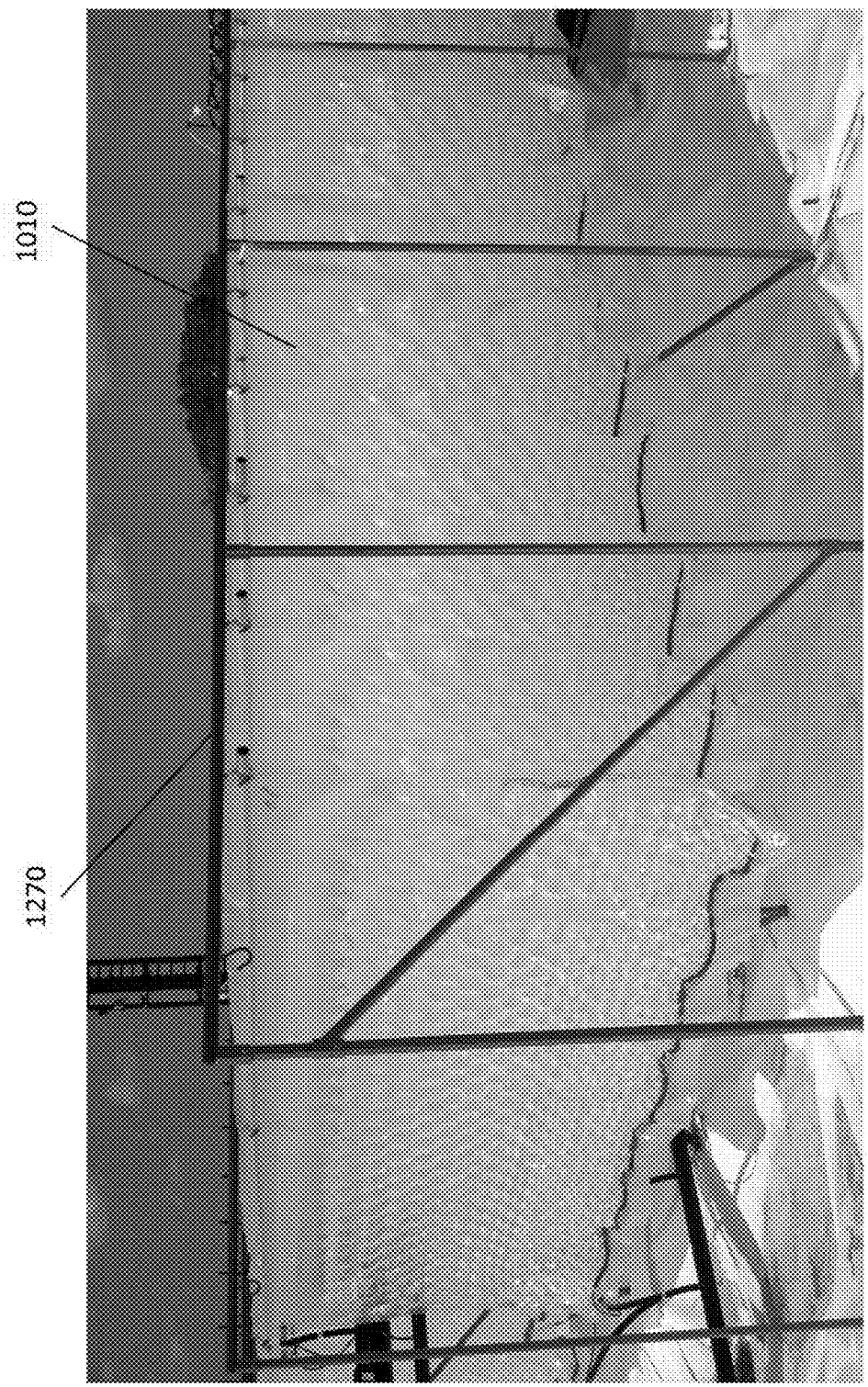
FIG. 11 shows a perspective view of a photobioreactor design and portions of a support structure of the present invention.

The support structure used to maintain the vertical orientation of the photobioreactor enclosure can incorporate any suitable components and materials that minimize cost while providing adequate support and stability considering the weight of the photobioreactor enclosure and contents and considering changing environmental conditions. As shown in FIGS. 9-11, in some embodiments, the photobioreactor enclosure is suspended above the ground from a horizontal beam 1250 supported at either end by horizontal supports 1270 that are supported by vertical supports 1260, forming a box-like framework. Such a framework can be scaled to accommodate and support multiple photobioreactor enclosures 1010 in an array. The components of the framework can comprise metal, wood, plastic, and any other materials that provide adequate strength and low cost.

During operation of a photobioreactor system 1000 of the present invention, in some embodiments, gas comprising carbon dioxide is sparged through a gas diffuser 1040 into the photobioreactor enclosure 1010 to provide a feed substrate for photosynthetic productive organisms 1070. In some embodiments, the addition of carbon dioxide is controlled to a predetermined set point for the concentration of carbon dioxide in the gas headspace 1080 above the culture.

In some embodiments, gas is vented periodically or continually from the photobioreactor enclosure 1010 to limit oxygen concentration in the gas headspace 1080 and to control gas pressure in the photobioreactor enclosure 1010 within a range that maintains proper geometry of the photobioreactor enclosure 1010 shape and structural integrity of the photobioreactor enclosure 1010. In some embodiments, the range is about 1 to about 40 inches of water. In some embodiments, the range is about 2 to about 6 inches of water.

Example 1

In a prophetic example, FIGS. 12-21 illustrate the seaming patterns in the exemplary vertical photobioreactor enclosure shown in FIG. 3 made of flexible film. Placements of seams and other structural features shown in FIGS. 3, 7 and 12-22 are drawn to scale in each Figure.

According to the present invention, in photobioreactor enclosures constructed using polyethylene film, the seaming patterns shown in FIGS. 3 and 12-21 distribute mechanical stresses in a manner that maintains substantially uniform thickness of the photobioreactor enclosure and minimizes or substantially eliminates formation of touch points, folds or creases in the walls of the photobioreactor enclosure that would inhibit flows of gas and liquid.

Additionally, the rounded corners 2062 of the photobioreactor enclosure shown in FIGS. 3 and 12-21 better facilitate flow of liquids and gases in the photobioreactor enclosure and facilitate complete flushing of the photobioreactor enclosure, for example when filling or draining the photobioreactor enclosure. When liquids are drained from the photobioreactor enclosure, the slope of the seamed edge 2060 at the bottom of the photobioreactor enclosure down to a liquid out port 2280 facilitates gravity draining. When the photobioreactor enclosure is filled with liquid, the slope of the seamed edge 2060 at the top of the photobioreactor enclosure up toward a gas out port 2270 helps expel gas from the photobioreactor enclosure and eliminate trapped gas bubbles.

Figure 12:
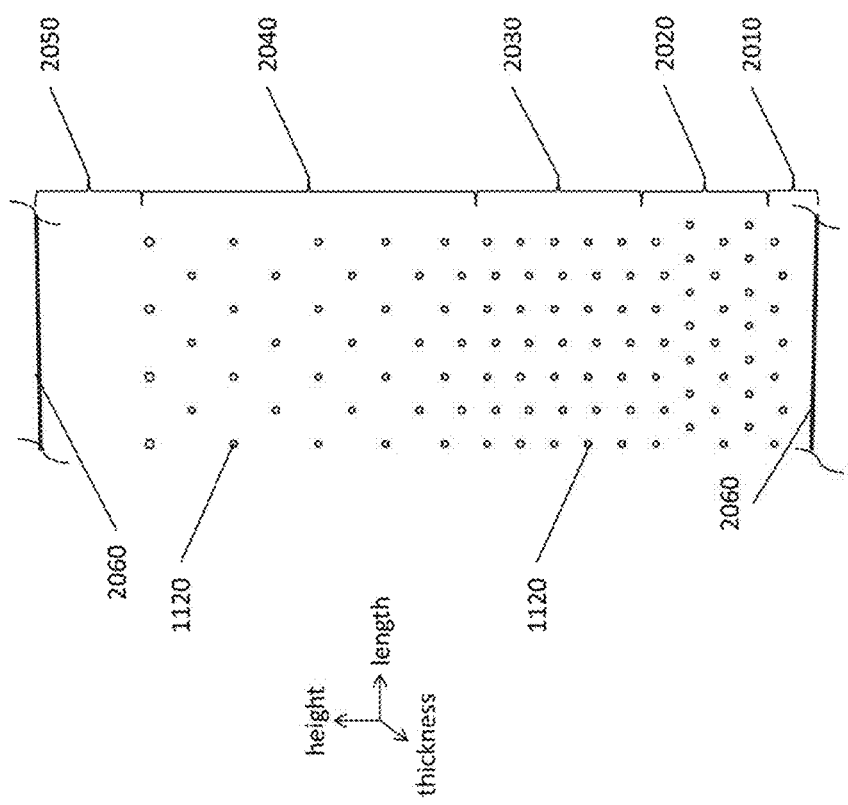
FIG. 12 shows a sectional plan view of a photobioreactor design of the present invention.

FIG. 12 shows a sectional view of horizontal regions 2010, 2020, 2030, 2040, 2050 of the photobioreactor enclosure shown in FIG. 3, increasing in vertical height from region 2010 to region 2050. A gas diffuser would be positioned in region 2010. A gas headspace region would be found in region 2050.

Each region experiences varying mechanical stress caused by aggregate weight and pressure head applied to a region. Aggregate weight of the photobioreactor enclosure and liquid suspended below a region decreases from higher regions, such as region 2050, to lower regions, such as region 2010. Pressure head from liquid filling the photobioreactor enclosure increases from higher regions, such as region 2050, to lower regions, such as region 2010. In a photobioreactor enclosure filled with about 48 liters of liquid to a fill height of about 36 inches, pressure head in region 2010 is about 34 to about 36 inches of water, pressure head in region 2020 is about 26 to about 34 inches of water, pressure head in region 2030 is about 17 to about 26 inches of water, and pressure head in region 2040 is about 0 to about 17 inches of water. The gas headspace region in region 2050 can be inflated to a pressure of, for example, about 10 inches of water.

Figure 13:
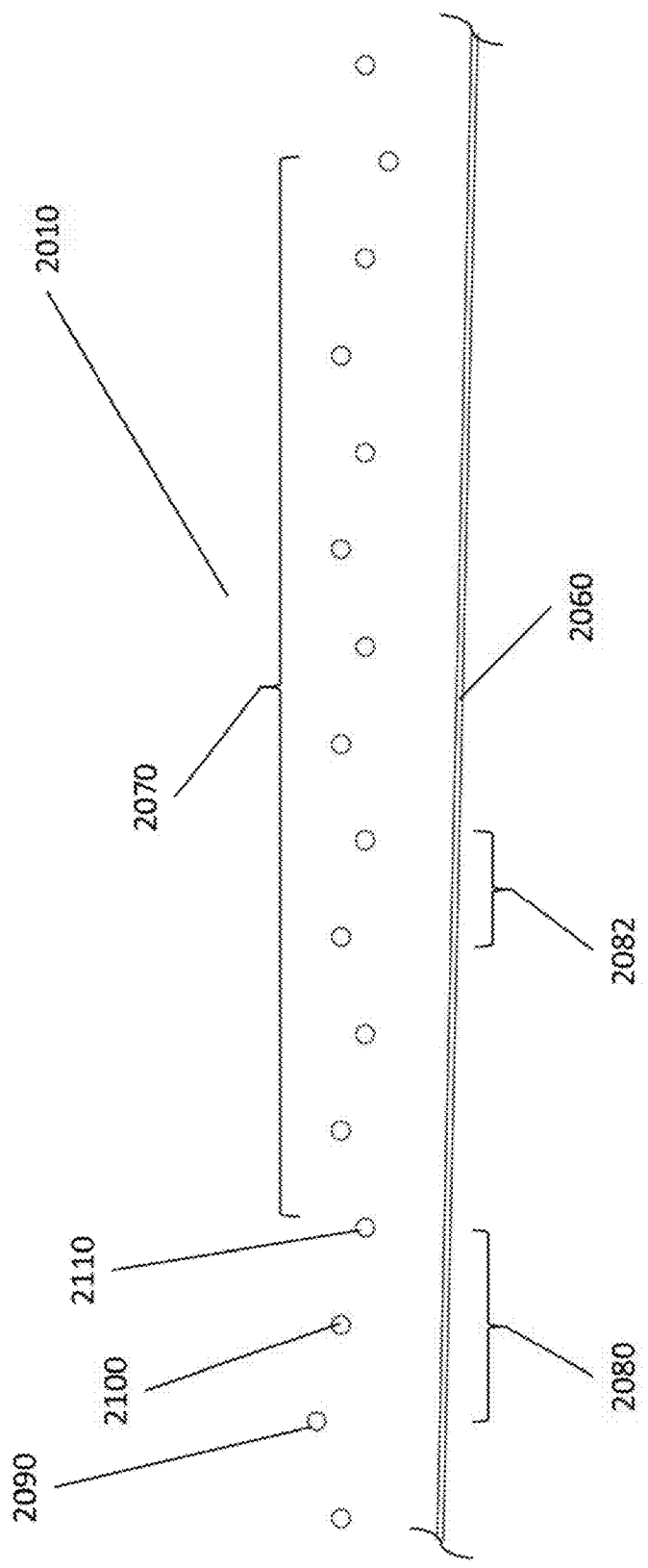
FIG. 13 shows a sectional plan view of a photobioreactor design of the present invention.

FIG. 13 shows arrangement of the point seams in region 2010. A weld along the perimeter of the photobioreactor enclosure forms the bottom, top and side edges 2060 of the photobioreactor enclosure. The bottom and top edges 2060 are sloped from horizontal. Pattern 2070 is 22 inches long and repeats 5 times over the length of the photobioreactor enclosure. Pattern 2070 comprises subpatterns 2080 and 2082. Point seams 2090 are positioned about 2.64 inches above the bottom edge 2060, and about 0.5 inches above point seam 2100. Pivot point seams 2110 are positioned about 1.55 inches above the bottom edge 2060, and about 0.5 inches below point seam 2100. Point seams 2080, 2090 and 2100 are spaced horizontally about 2 inches between each point seam. The arrangement of point seams in region 2010 provides a sufficiently large void volume in the photobioreactor enclosure to allow insertion of a gas diffuser tube and enable full draining of liquids with a gas diffuser tube in place.

Figure 14:
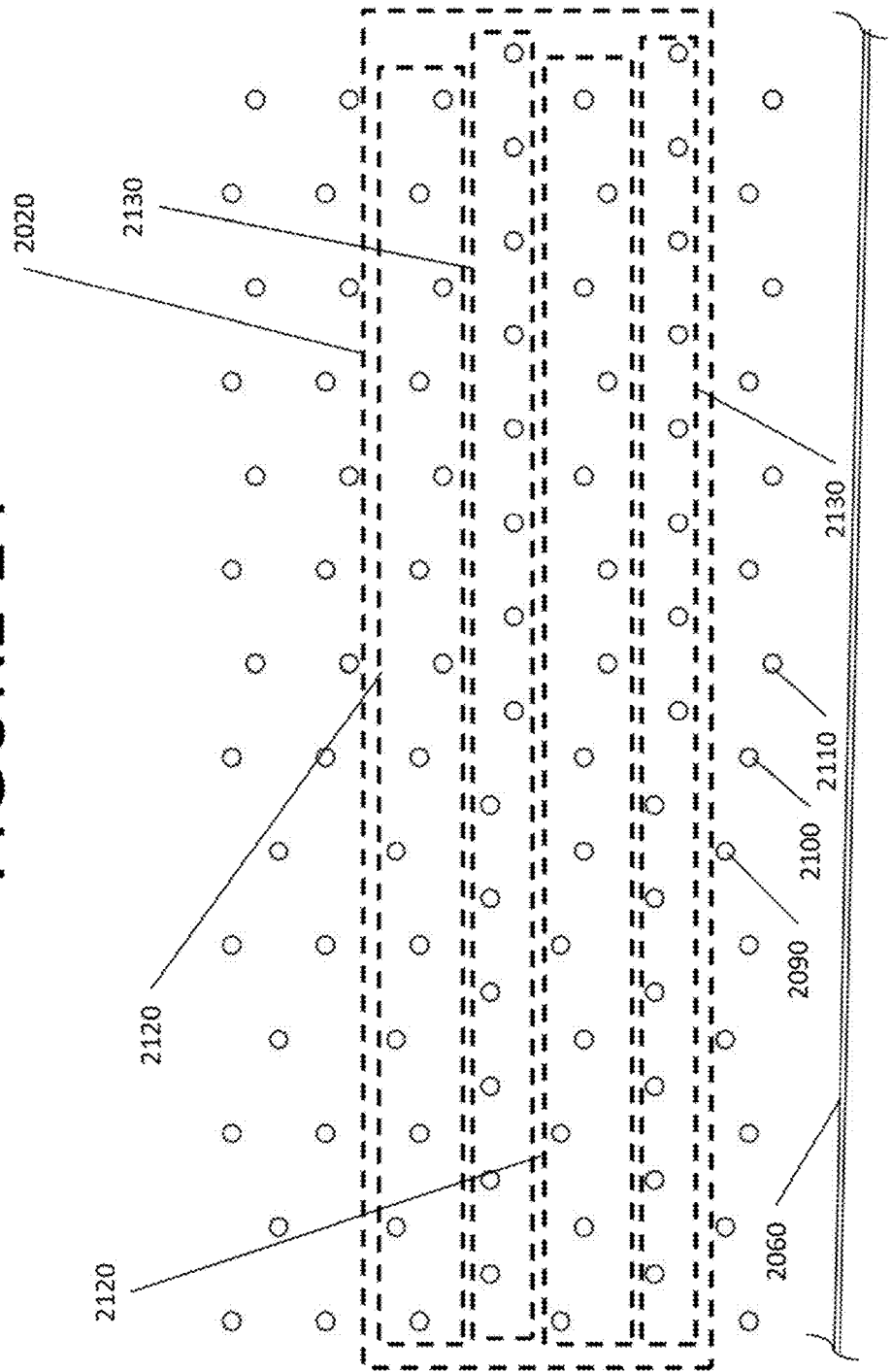
FIG. 14 shows a sectional plan view of a photobioreactor design of the present invention.
Figure 15:
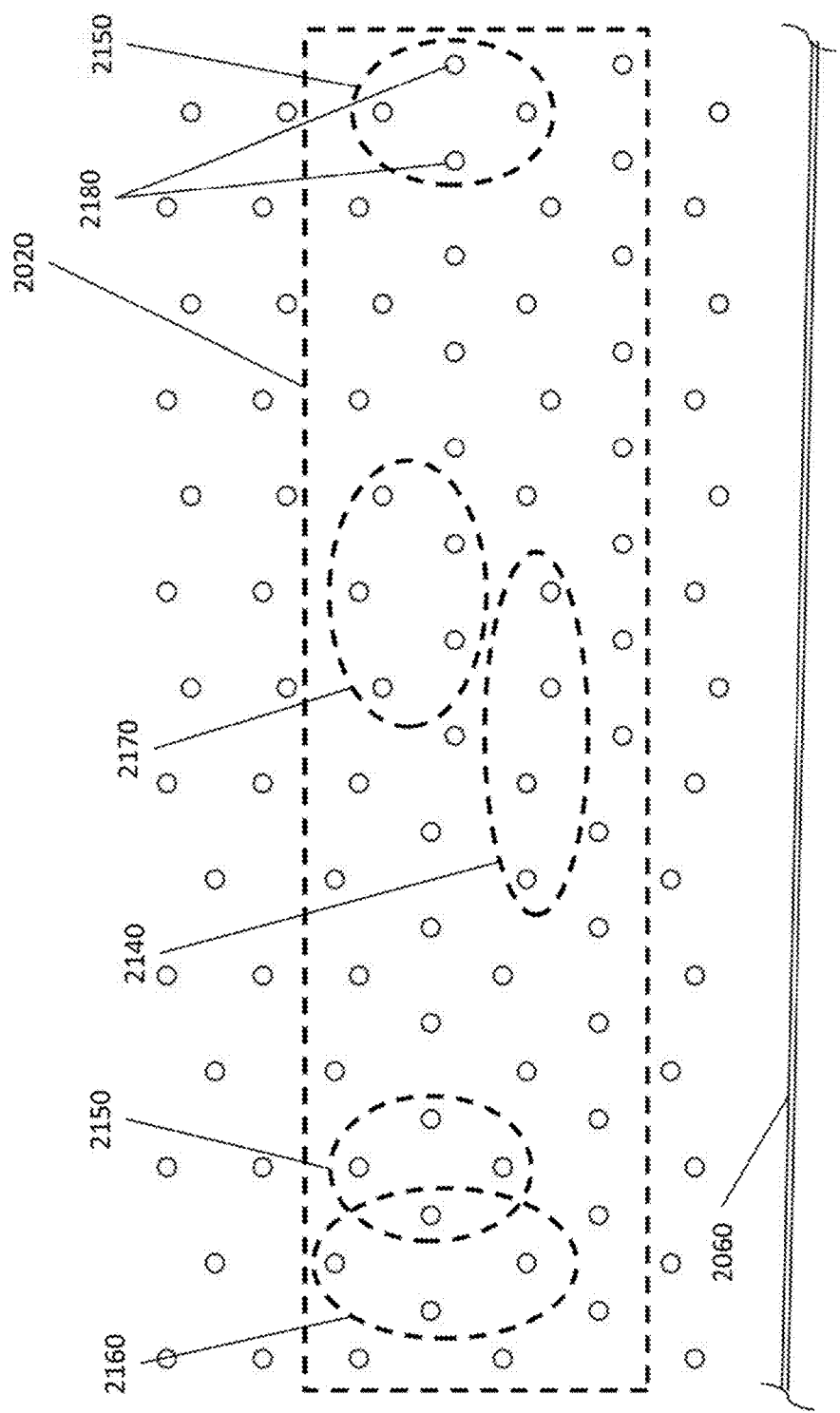
FIG. 15 shows a sectional plan view of a photobioreactor design of the present invention.

FIGS. 14 and 15 show point seaming patterns in region 2020 of the photobioreactor enclosure. Point seams in rows 2120 are spaced apart vertically about 0.5 inches and horizontally about 2 inches. Point seams in rows 2130 are spaced apart horizontally about 2 inches, and the height difference, identified in portion 2140, between segments of point seams in rows 2130 is about 0.5 inches. Point seams in rows 2130 are spaced vertically from the point seams in rows 2120 by about 1.5 or about 2 inches and horizontally by about 1 inch.

Region 2020 includes point seams arranged in diamond patterns 2150, 2160 and five-point patterns 2170 that repeat across the length of the photobioreactor enclosure. Horizontal spacing of point seams 2180 in the diamond patterns 2150, 2160 is about 2 inches.

Figure 16:
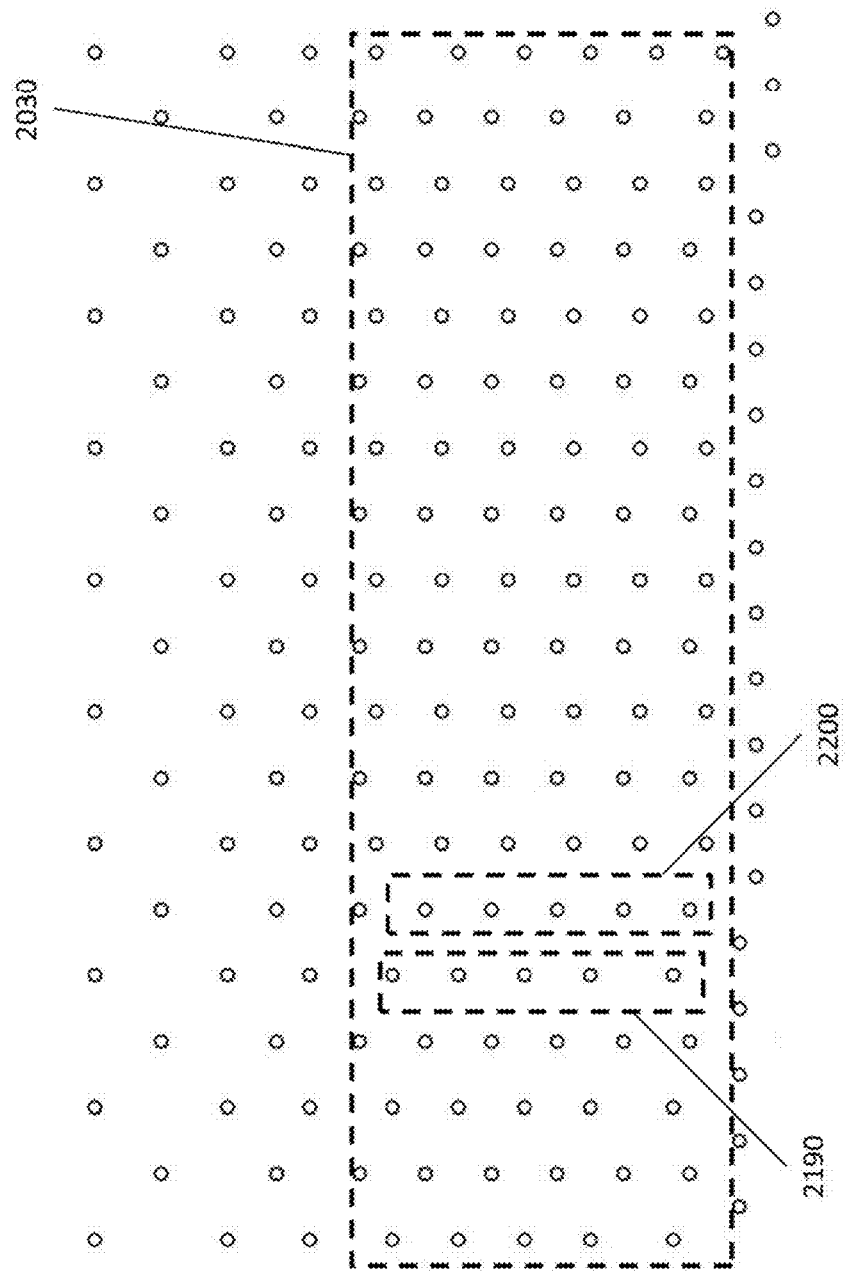
FIG. 16 shows a sectional plan view of a photobioreactor design of the present invention.

FIG. 16 shows the spacing and arrangement of point seams in region 2030 of the photobioreactor enclosure. Vertical spacing between point seams in column 2190 and column 2200 is about 0.5 to about 1.5 inches. Vertical spacing between point seams in either column 2190 or column 2200 is about 1.5 to about 2 inches. Horizontal spacing between column 2190 and column 2200 is about 2 inches.

Figure 17:
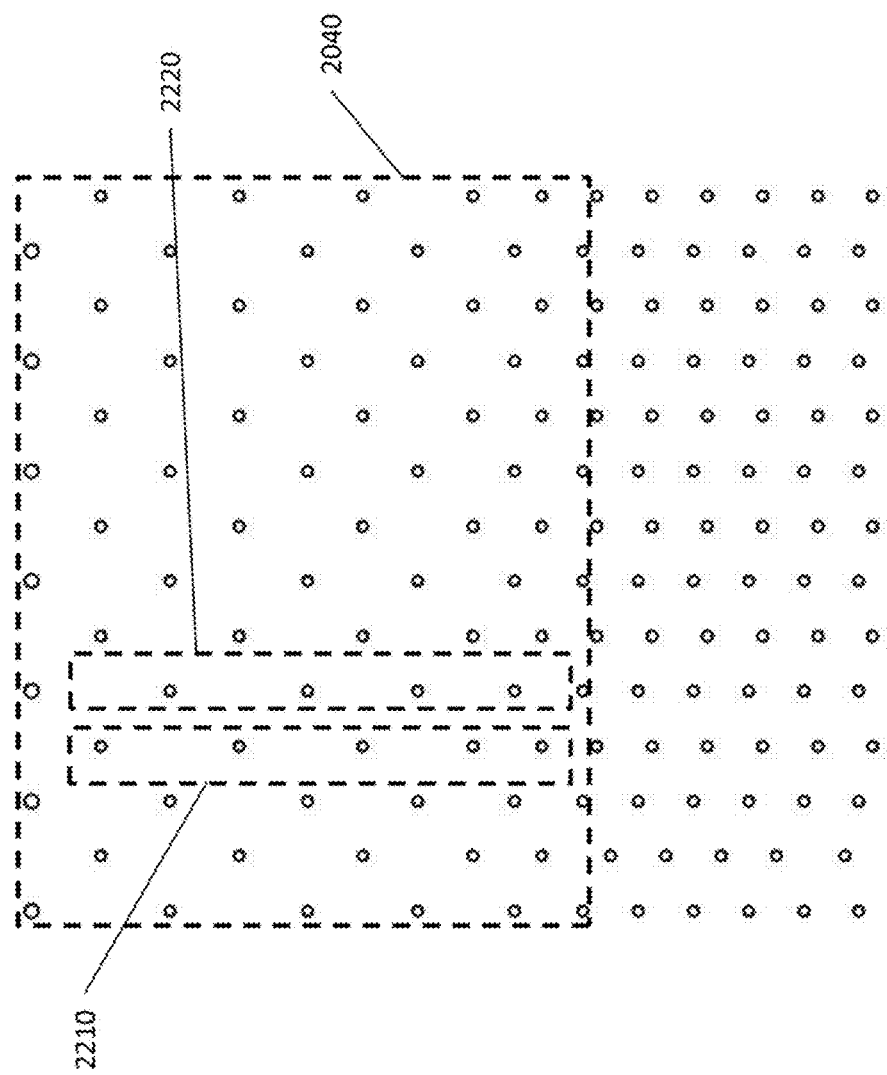
FIG. 17 shows a sectional plan view of a photobioreactor design of the present invention.

FIG. 17 shows the spacing and arrangement of point seams in region 2040 of the photobioreactor enclosure. Vertical spacing between point seams in column 2210 and column 2220 is about 1.5 to about 3 inches. Vertical spacing between point seams in either column 2210 or column 2220 is about 2.5 to about 5.5 inches. Horizontal spacing between column 2210 and column 2220 is about 2 inches.

Figure 18:
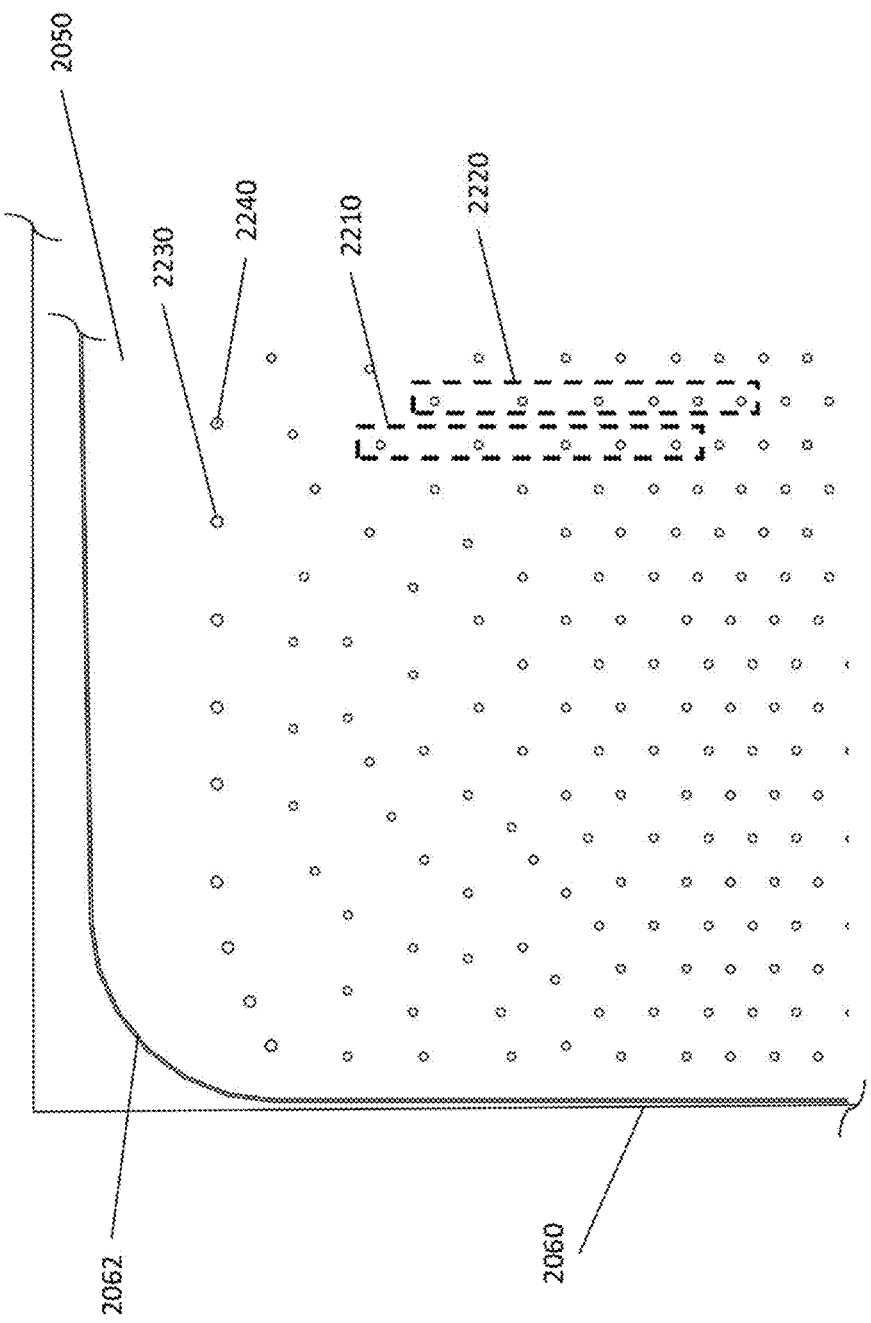
FIG. 18 shows a sectional plan view of a photobioreactor design of the present invention.
Figure 19:
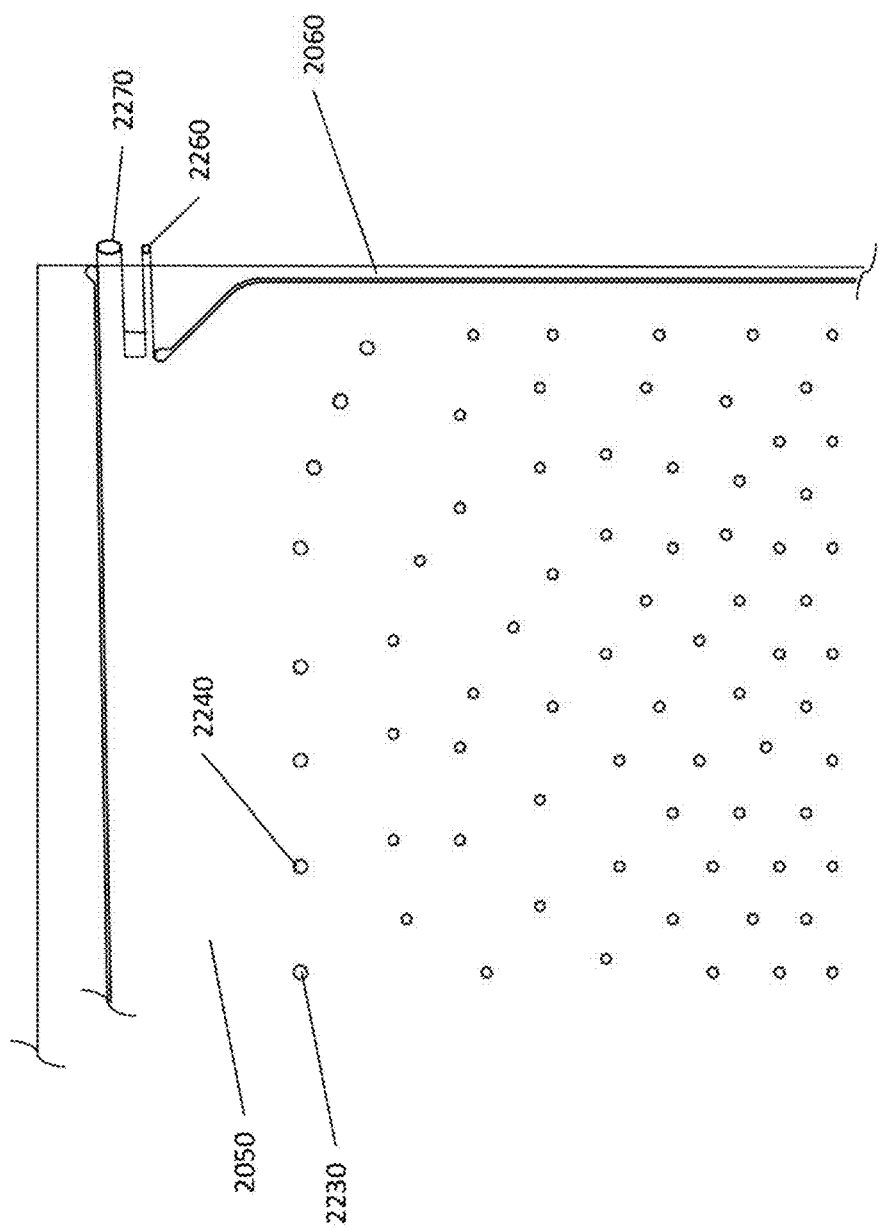
FIG. 19 shows a sectional plan view of a photobioreactor design of the present invention.
Figure 20:
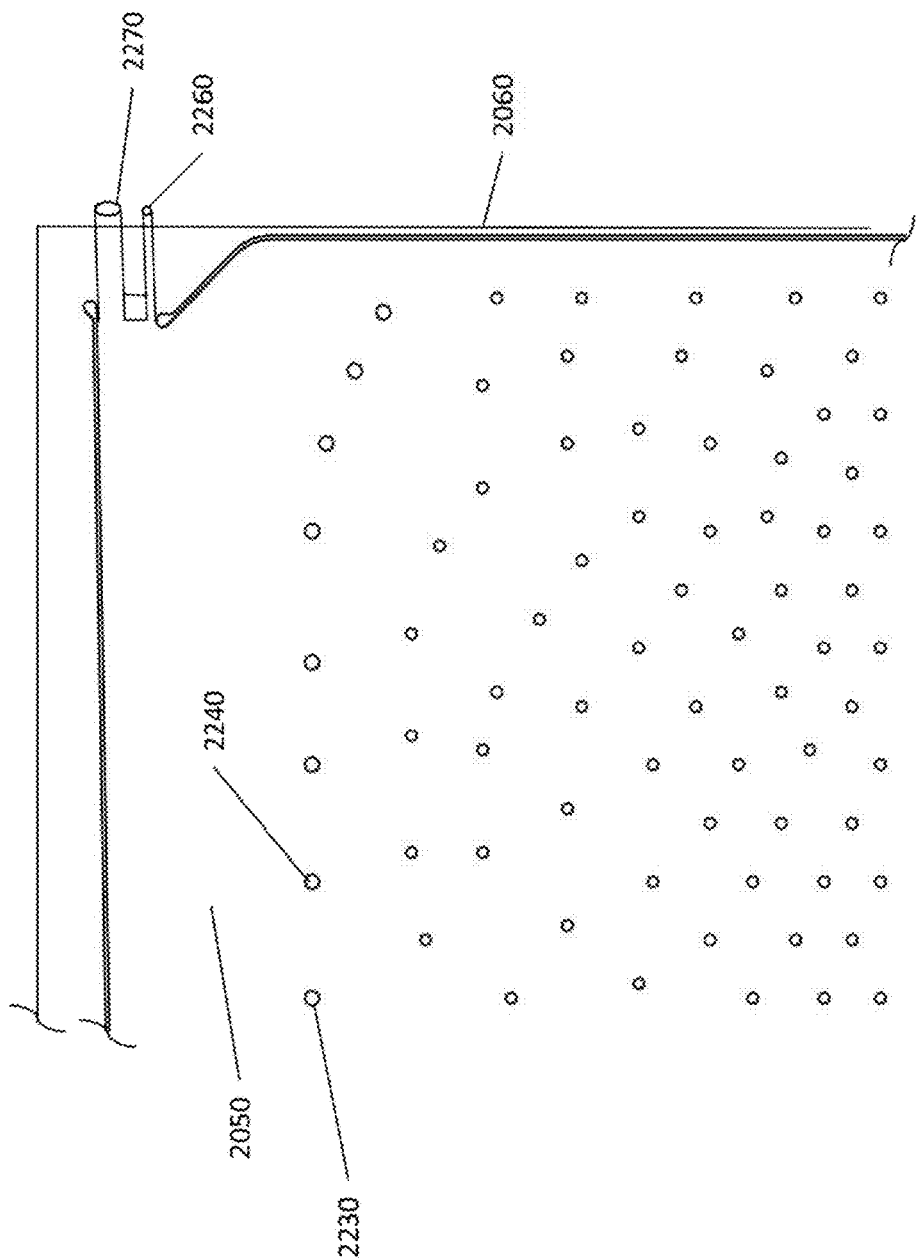
FIG. 20 shows a sectional plan view of a photobioreactor design of the present invention.

FIGS. 18-20 show the spacing and arrangement of point seams in region 2050 of the photobioreactor enclosure. Horizontal spacing between point seams 2230 and 2240 is about 4 inches. As shown in FIG. 19, liquid in ports 2260 and gas out ports 2270 positioned in the corner connect with the void volume of the photobioreactor enclosure about 3 inches from the edge of the photobioreactor enclosure. This configuration minimizes rotation or movement of the ports in the direction of the thickness of the photobioreactor enclosure. In an alternative embodiment shown in FIG. 20, a polyethylene weld above a port does not extend to the edge of the photobioreactor enclosure, which allows the port to angle upwards when filling the photobioreactor enclosure.

Figure 21:
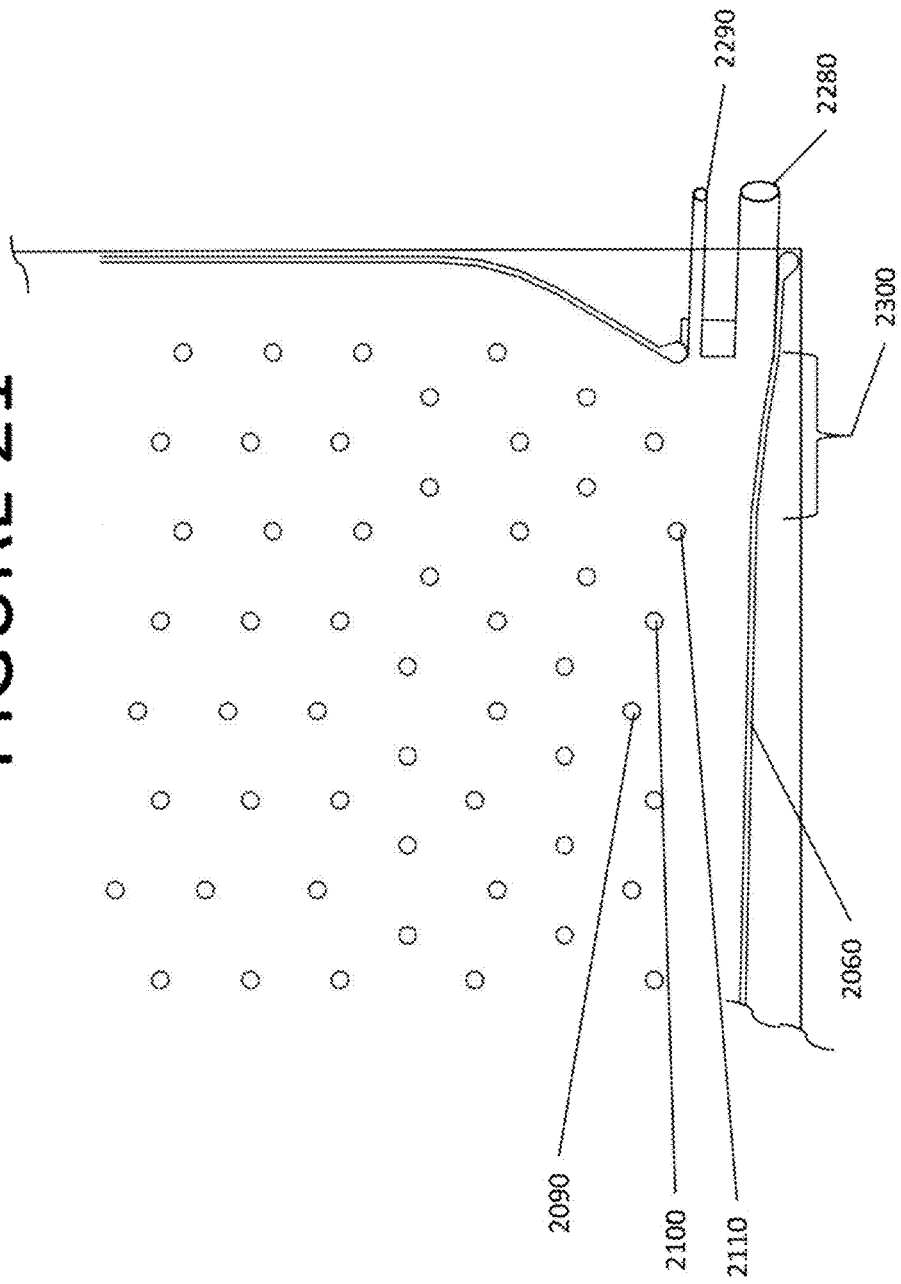
FIG. 21 shows a sectional plan view of a photobioreactor design of the present invention.

As shown in FIG. 21, liquid out ports 2280 and gas in ports 2290 of the photobioreactor enclosure connect with the void volume of the photobioreactor enclosure about 3 inches from the edge of the photobioreactor enclosure, in order to minimize rotation or movement of the ports in the direction of the thickness of the photobioreactor enclosure. A sump 2300 links the bottom edge of the photobioreactor enclosure with the liquid out port to allow for better draining and provides a height difference of about 0.5 inches between the bottom edge 2060 of the photobioreactor enclosure and the liquid out port 2280.

Diameter of the point seams in FIGS. 3 and 12-21 is 0.375 inches, except that diameter of the uppermost point seams that would be covered by liquid in the photobioreactor enclosure is 0.5 inches. Additional point seams in the gas headspace of the photobioreactor enclosure may be 0.5 inches or more in diameter.

The bottom and top edges of the photobioreactor enclosure may be sloped, for example, about 2% from horizontal in order to improve filling and draining of the photobioreactor enclosure with liquid and gas.

Inner diameter of the liquid and gas in ports may be about 0.125 inches. Inner diameter of the liquid and gas out ports may be about 0.625 inches.

Corner angles in the photobioreactor enclosure may be greater than 90 degrees.

Figure 22:
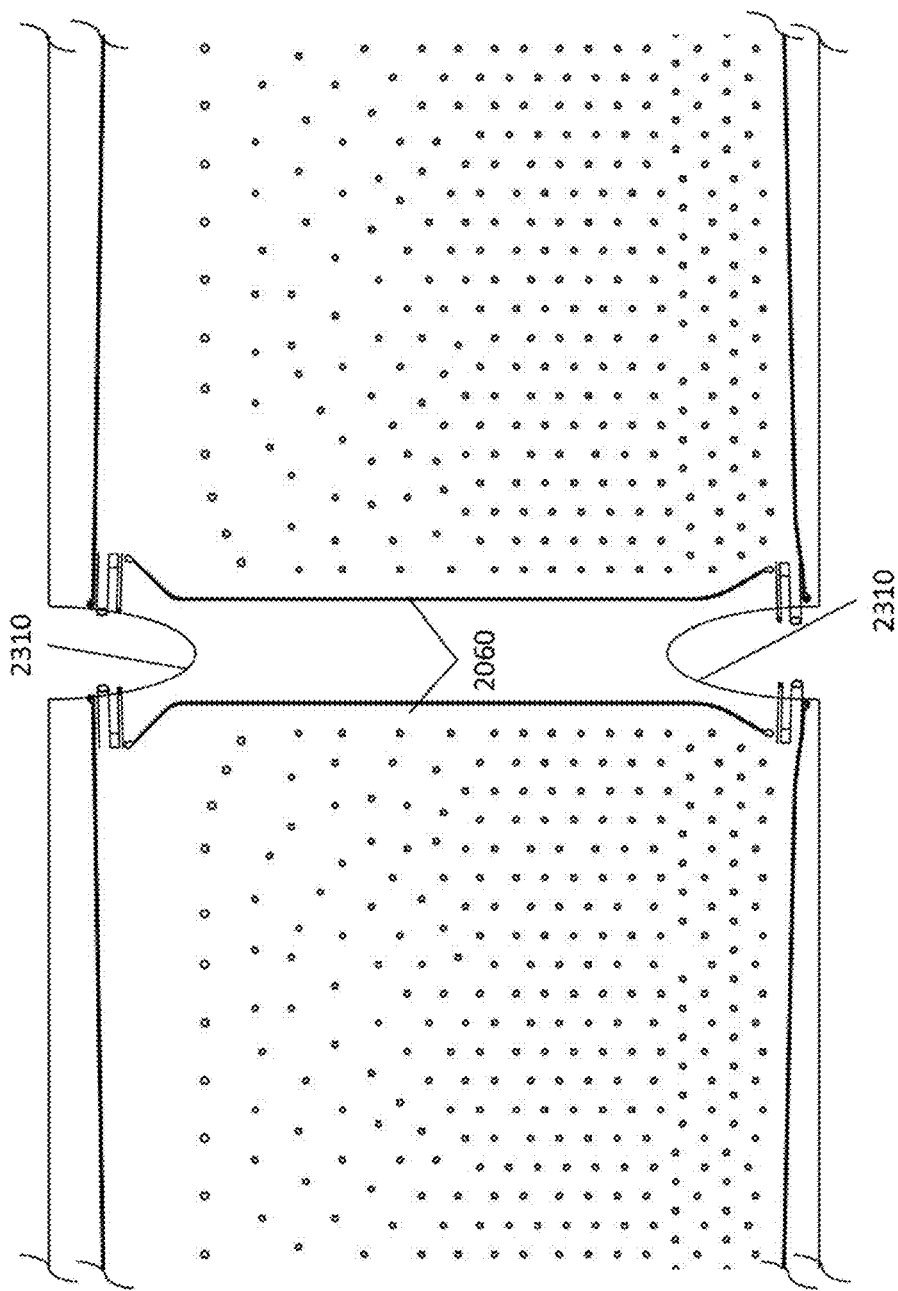
FIG. 22 shows a sectional plan view of a photobioreactor design of the present invention.

FIG. 22 shows an embodiment in which two photobioreactor enclosures are joined by a section of flexible film connecting side edges 2060 of the enclosures, with cut outs 2310 formed in the section of flexible film to facilitate connection of piping or tubing to the ports.

Example 2

In a prophetic example, vertically-oriented and horizontally-oriented photobioreactors constructed of flexible film, such as polyethylene, are inoculated with liquid cultures of various productive organisms that are genetically transformed through the addition of various enzymes to make ethanol and that are exposed to photosynthetically active radiation within the photobioreactors.

In some embodiments, horizontally-oriented photobioreactor enclosures are configured and operated according to known art, for example, U.S. Pat. No. 8,323,958. Air is bubbled into a horizontally-oriented photobioreactor enclosure by sparging, with addition of carbon dioxide to control pH of the liquid culture to a setpoint of 7.0.

In some embodiments, vertically-oriented photobioreactor enclosures comprise vertical partitions 1050 that form channels 1090 in the photobioreactor enclosure 1010, as shown in FIG. 5. The partitions 1050 may be created by, for example, bonding together portions of the opposing walls 1060 to create seams that extend the full height of the photobioreactor enclosure 1010 or a portion of the height of the photobioreactor enclosure 1010.

Photobioreactor enclosures corresponding to FIG. 5 are about 24 inches long, about 36 inches tall, about 2.6 cm thick and are filled with the culture of productive organisms to a height of about 2 feet and volume of about 17 liters. Gas is sparged into the photobioreactor enclosures with a tubular gas diffuser made of ethylene propylene diene monomer foam rubber and having about 16 perforations per inch across the length of the gas diffuser tube.

In some embodiments, vertically-oriented photobioreactor enclosures comprise patterns of point seams shown in FIG. 3 or FIG. 7.

Photobioreactor enclosures corresponding to FIG. 7 are about 114 inches long, about 54 inches tall, about 2.25 cm thick and are filled with the culture of productive organisms to a height of about three feet and volume of about 57 liters. Each photobioreactor enclosure incorporates a downcomer channel formed by internal seams. Gas is sparged into the photobioreactor enclosures with a tubular gas diffuser made of ethylene propylene diene monomer foam rubber and having about 12 perforations per inch across the length of the gas diffuser tube.

Photobioreactor enclosures corresponding to FIG. 3 are about 114 inches long, about 54 inches tall, about 1.8 cm thick and are filled with the culture of productive organisms to a height of about three feet and volume of about 48 liters. Gas is sparged into the photobioreactor enclosures with a tubular gas diffuser made of ethylene propylene diene monomer foam rubber and having a pattern of perforated and non-perforated sections shown in FIG. 6, creating alternating zones of gas bubbling and no bubbling. The non-perforated sections are about 1.5 inches or about 3 inches long. The perforated sections are about 15 inches long, with about 4 perforations per inch.

A suitable flow rate of sparge gas into the vertically-oriented photobioreactor enclosures is about 1.5 to about 2.0 SLPM. Carbon dioxide concentration in the head space of the vertically-oriented photobioreactor enclosures is used for feedback control of carbon dioxide injection. The carbon dioxide injection concentration is set at, for example, about 10% of the air flow rate, and the injection frequency is controlled to brief pulses. Delivery of carbon dioxide is controlled to concentration set points of, for example, about 2% during the day and about 1% during the night.

Gas is vented from the photobioreactor enclosures to remove oxygen. A portion of gas may be recirculated to the photobioreactor enclosure.

Figure 23:
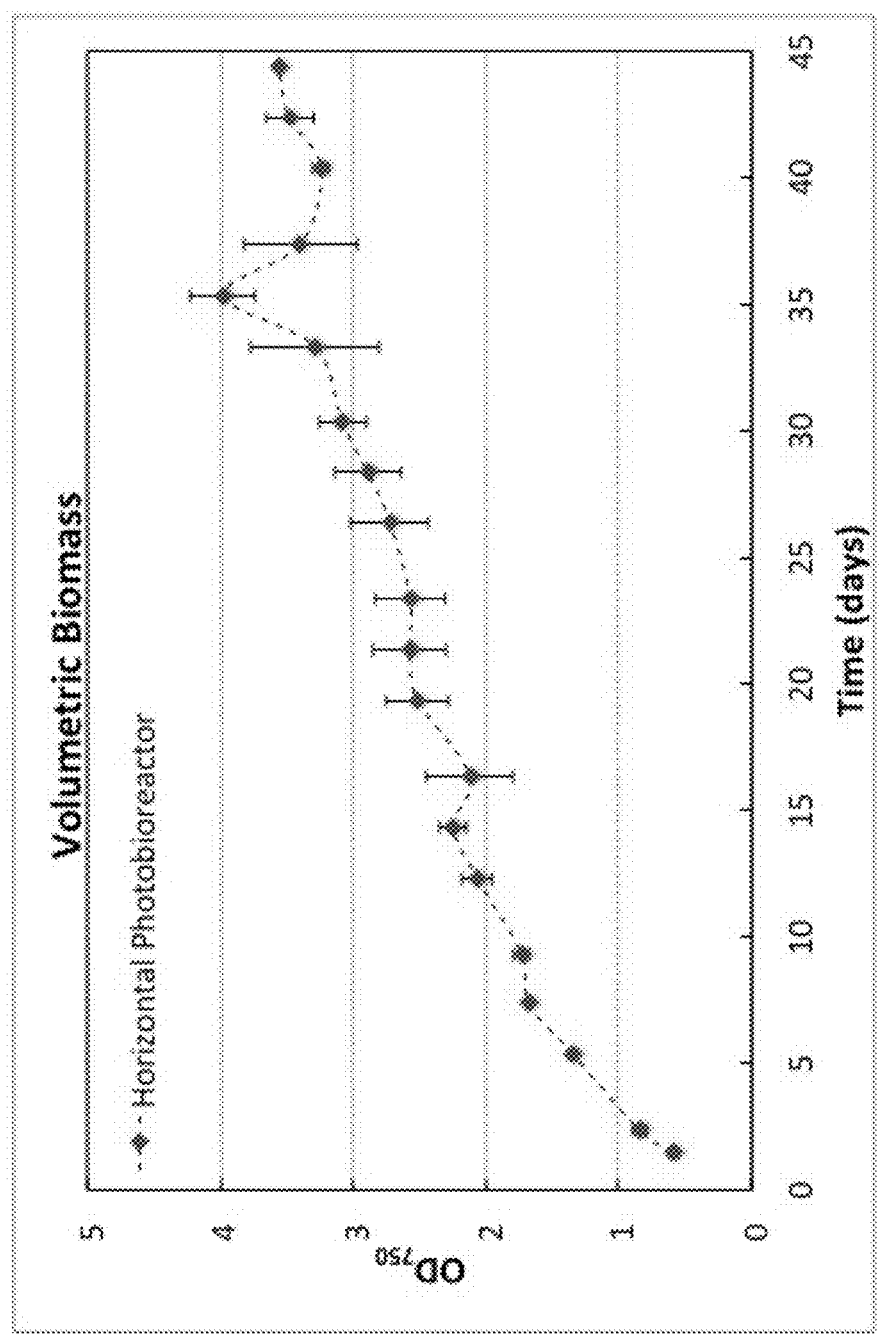
FIG. 23 shows volumetric biomass production.
Figure 24:
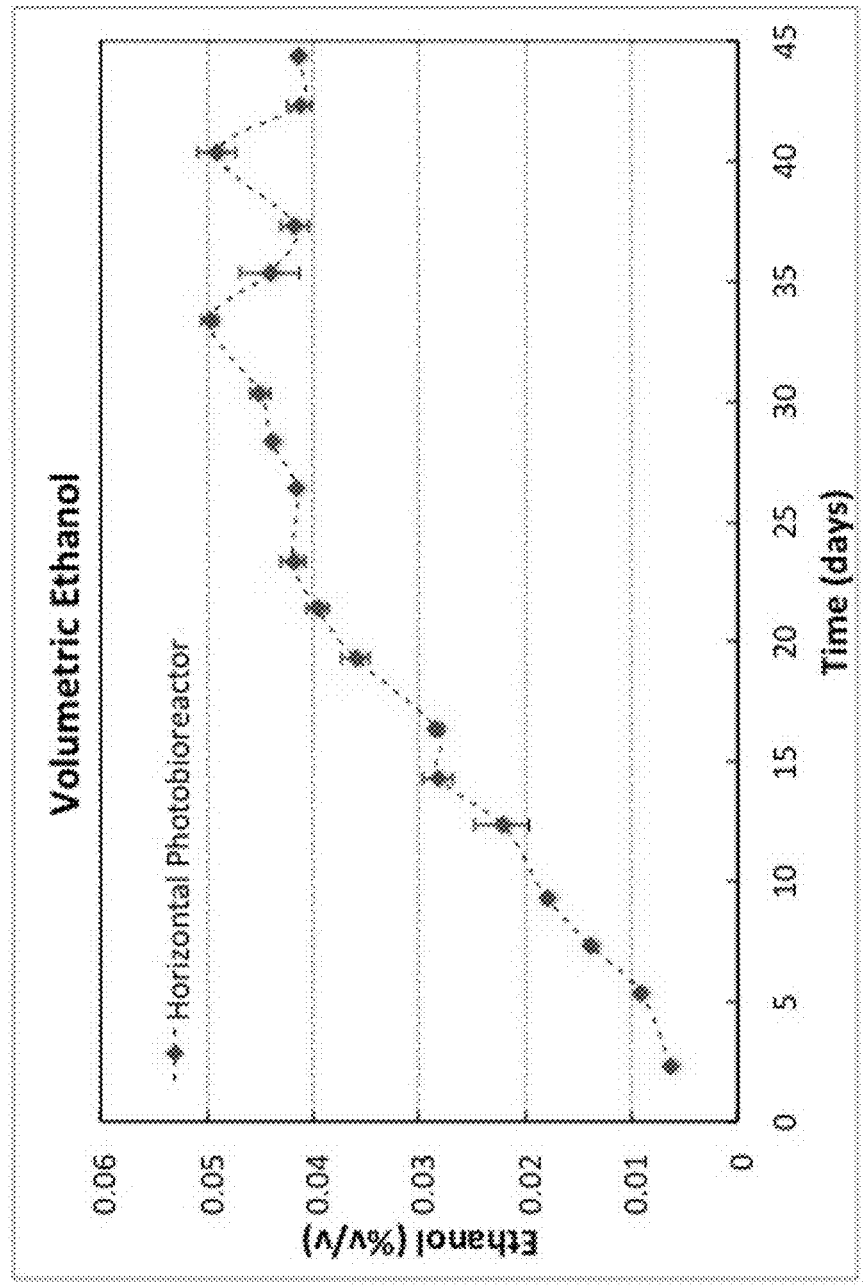
FIG. 24 shows volumetric ethanol production.

FIGS. 23 and 24 show exemplary volumetric biomass accumulation and volumetric ethanol production, respectively, for horizontally-oriented photobioreactors.

Figure 25:
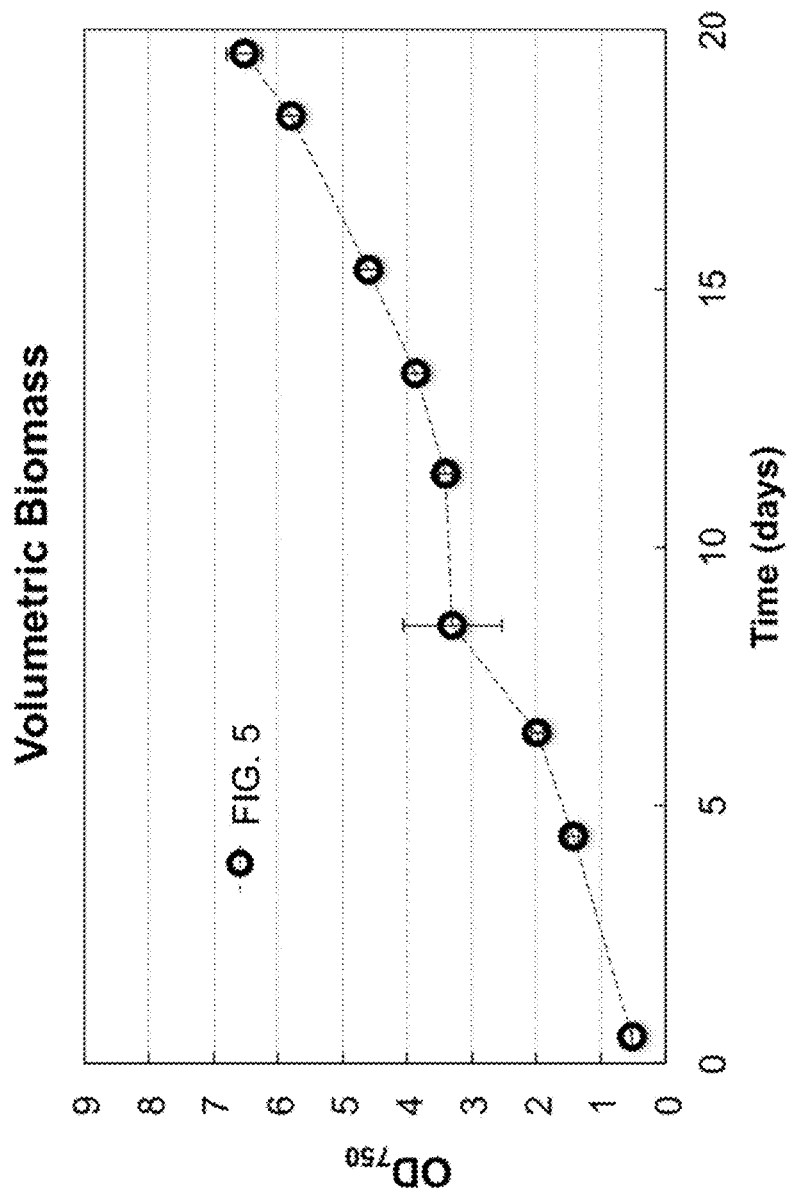
FIG. 25 shows volumetric biomass production.
Figure 26:
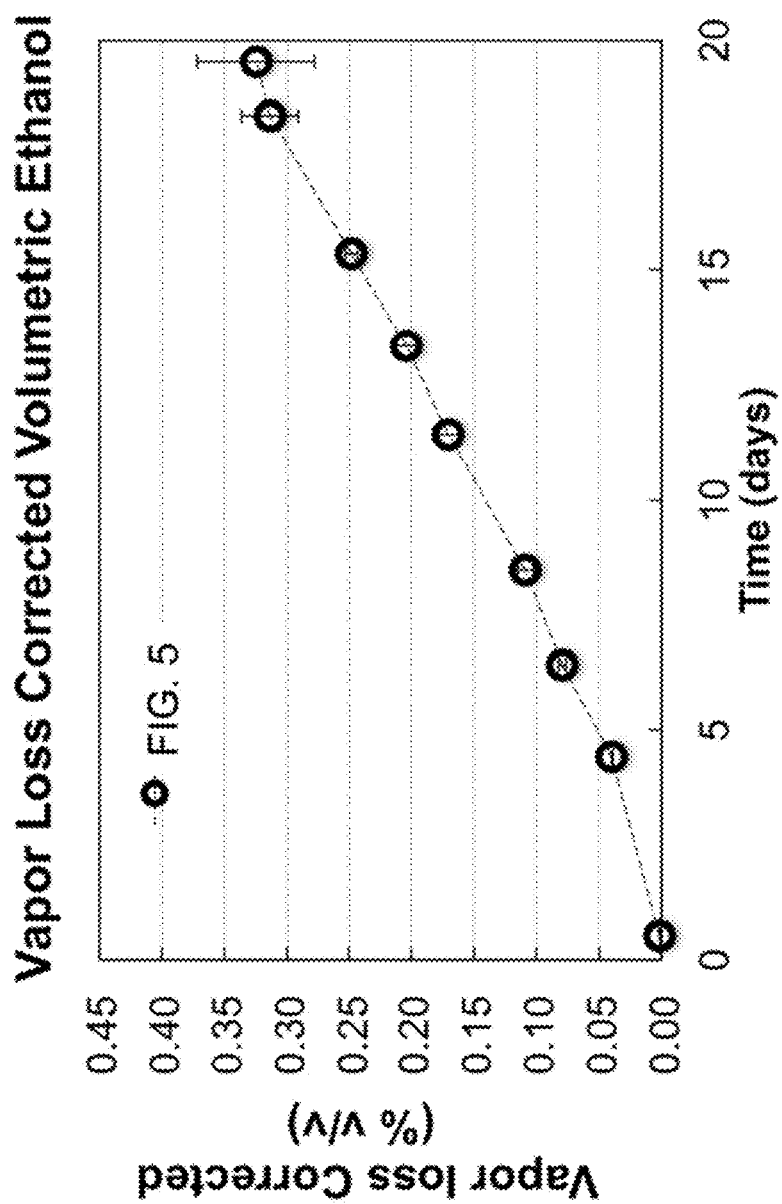
FIG. 26 shows volumetric ethanol production.

FIGS. 25 and 26 show exemplary volumetric biomass accumulation and volumetric ethanol production, respectively, for vertically-oriented photobioreactors comprising vertical partitions as shown in FIG. 5.

Figure 27:
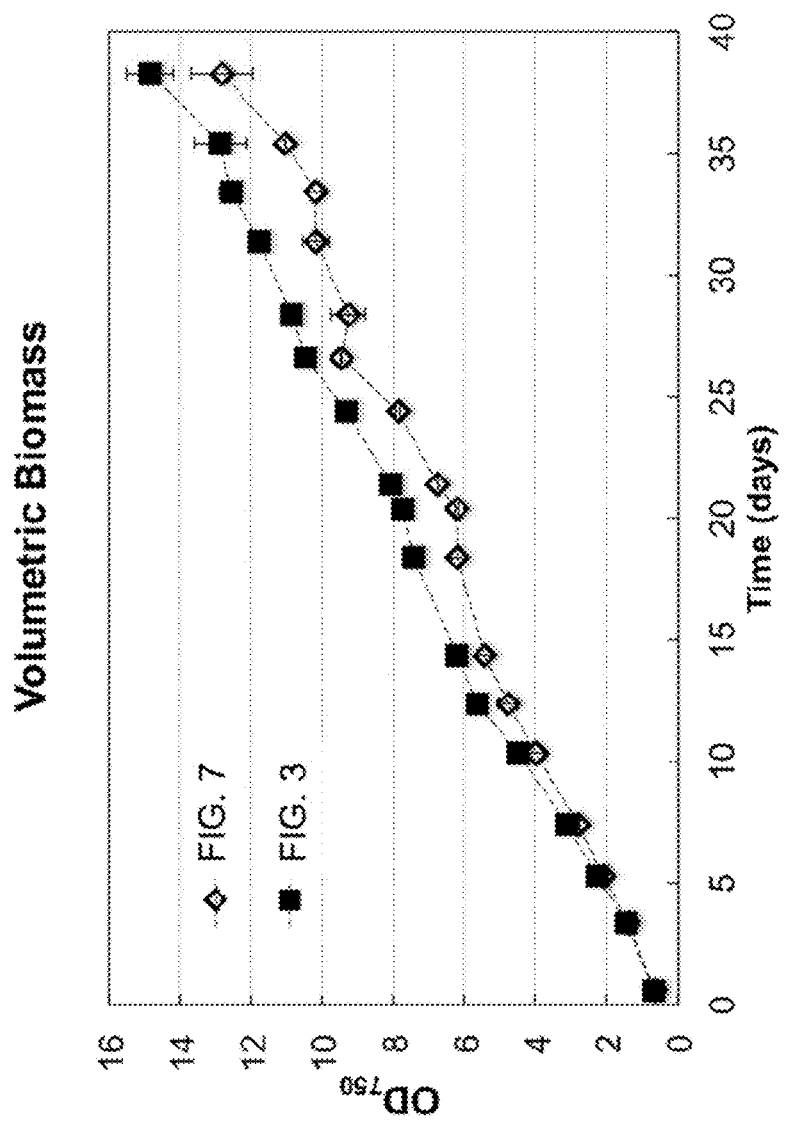
FIG. 27 shows volumetric biomass production.
Figure 28:
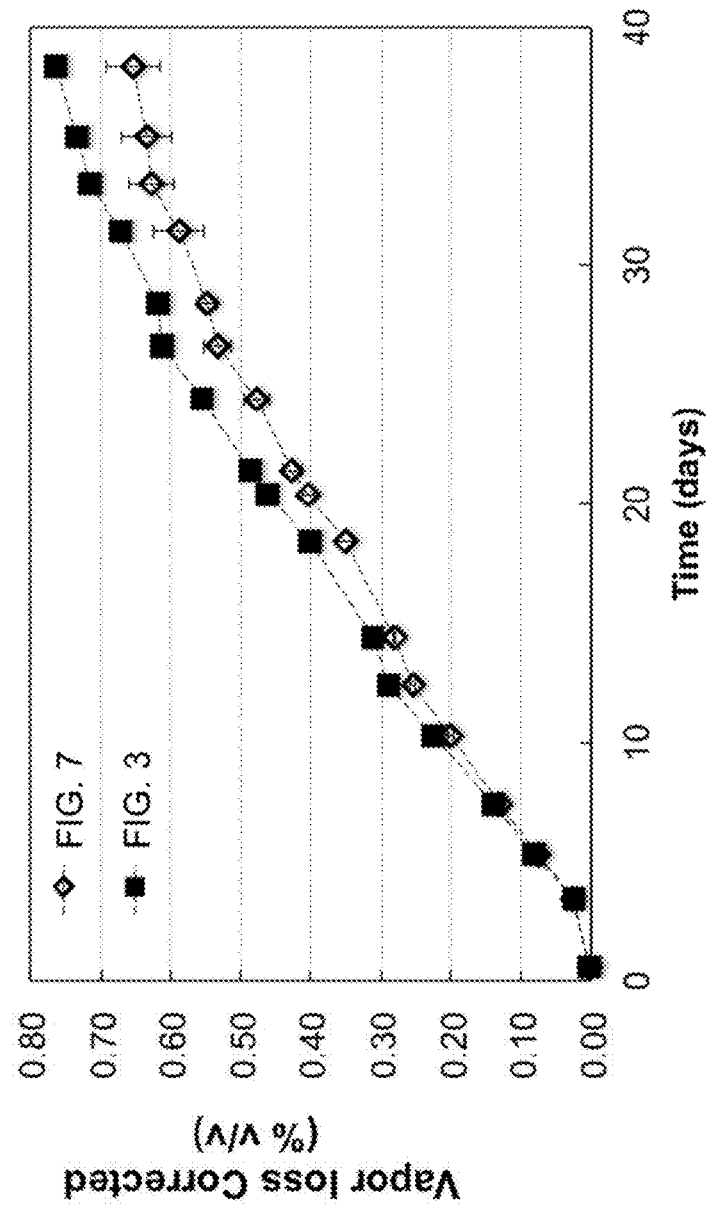
FIG. 28 shows volumetric ethanol production.

FIGS. 27 and 28 show exemplary volumetric biomass accumulation and volumetric ethanol production, respectively, for vertically-oriented photobioreactors comprising patterns of point seams as shown in FIGS. 3 and 7.

While the embodiments of the invention disclosed herein are presently considered to be preferred, various changes and modifications can be made without departing from the scope of the invention. The scope of the invention is indicated in the appended claims, and all changes that come within the meaning and range of equivalents are intended to be embraced therein.

What is claimed is:

1. A photobioreactor for culturing productive organisms comprising:
    a) an enclosure capable of housing a liquid culture of productive organisms and a gas headspace above the liquid culture, wherein the enclosure comprises top, bottom and side edges, a height oriented substantially vertically, a length, a thickness less than either of the height or the length, and a flexible film, at least one portion of the flexible film being translucent;

b) a plurality of point seams formed in the enclosure, scaled to the pattern of all point seams shown in FIG. 3 or to the pattern of all point seams shown in FIG. 7;

c) a gas diffuser disposed in a lower portion of the enclosure below the plurality of point seams and capable of introducing gas into the enclosure; and d) a plurality of ports formed in the enclosure.

2. The photobioreactor of claim 1, wherein the enclosure has a length of from about 110 to about 120 inches, a height of from about 50 to about 60 inches, and an average thickness of from about 1.5 to about 2.5 centimeters, further wherein the plurality of point seams have diameters or widths of about 0.75 inches or less, further wherein the pattern shown in FIG. 7 comprises a downcomer channel.

3. The photobioreactor of claim 2, wherein the gas diffuser comprises a tubular shape comprising ethylene propylene diene monomer, the gas diffuser further comprising a length at least about 5 inches less than the length of the enclosure, an inner diameter of from about 0.1 to about 0.25 inches, and a pattern of perforations corresponding to and scaled to all perforations shown in FIG. 6.

4. A photobioreactor system comprising the photobioreactor in claim 3, further comprising a first header, a second header, a third header and a fourth header in fluid communication with the enclosure through the plurality of ports, wherein the enclosure is filled with the liquid culture from the bottom edge of the enclosure to a fill height and the first header and the second header are positioned above the fill height, the third header is positioned below the fill height and above the bottom edge of the enclosure, and the fourth header is positioned below the bottom edge of the enclosure.

5. The photobioreactor system of claim 4, wherein ports for liquid addition and gas venting are formed in the top edge of the enclosure near a side edge of the enclosure.

6. The photobioreactor system of claim 4, further comprising a support structure comprising vertical and horizontal supports, wherein the photobioreactor and the first header, second header, third header and fourth header are suspended from the support structure.

7. A method of culturing productive organisms comprising the steps of:

a) inoculating the photobioreactor of claim 1 with a liquid culture of productive organisms;

b) exposing the liquid culture of productive organisms to photosynthetically active radiation;

c) adding carbon dioxide to the enclosure through the gas diffuser; and d) removing oxygen from the enclosure through at least one of the plurality of ports.

8. The method of claim 7, further comprising:

a. controlling concentration of carbon dioxide in the gas headspace to a preselected value through the addition of carbon dioxide to the enclosure; and b. controlling gas pressure inside the enclosure within a range from about 2 to about 6 inches of water by venting or adding gas through at least one of the plurality of ports.

9. The method of claim 8, wherein the liquid culture of productive organisms produces biomass, further comprising removing the biomass from the enclosure.

10. The method of claim 8, wherein the liquid culture of productive organisms produces a biofuel, further comprising removing the biofuel from the enclosure.

11. A photobioreactor for culturing productive organisms comprising:

a. an enclosure capable of housing a liquid culture of productive organisms and a gas headspace above the liquid culture, wherein the enclosure comprises top, bottom and side edges, wherein the bottom edge is sloped from horizontal, a height oriented substantially vertically, a length, a thickness less than either of the height or the length, and a flexible film, at least one portion of the flexible film being translucent;

b. a plurality of point seams spaced apart lengthwise about 2 inches between adjacent point seams and forming a first pattern in the enclosure, wherein the first pattern comprises a first subpattern [2080] and a second subpattern [2082], further wherein the first subpattern [2080] comprises a first point seam [2090] about 2.64 inches above the bottom edge, a second point seam [2100] about 0.5 inches below the first point seam, and a third point seam [2110] about 0.5 inches below the second point seam, further wherein the second subpattern [2082] comprises a fourth point seam from about 2.0 inches above the bottom edge and a fifth point seam about 0.5 inches below the fourth point seam;

c. a gas diffuser disposed in a lower portion of the enclosure below the plurality of point seams and capable of introducing gas into the enclosure; and d. a plurality of ports formed in the enclosure.

12. The photobioreactor of claim 11, wherein the enclosure has a length of from about 110 to about 120 inches, a height of from about 50 to about 60 inches, and an average thickness of from about 1.5 to about 2.5 centimeters, further wherein the plurality of point seams have diameters or widths of about 0.75 inches or less.

13. A photobioreactor system comprising the photobioreactor in claim 12, further comprising a first header, a second header, a third header and a fourth header in fluid communication with the enclosure through the plurality of ports, wherein the enclosure is filled with the liquid culture from the bottom edge of the enclosure to a fill height and the first header and the second header are positioned above the fill height, the third header is positioned below the fill height and above the bottom edge of the enclosure, and the fourth header is positioned below the bottom edge of the enclosure.

14. A method of culturing productive organisms comprising the steps of:

a. inoculating the photobioreactor of claim 11 with a liquid culture of productive organisms;

b. exposing the liquid culture of productive organisms to photosynthetically active radiation;

c. adding carbon dioxide to the enclosure through the gas diffuser; and d. removing oxygen from the enclosure through at least one of the plurality of ports.

15. The method of claim 14, further comprising:

a. controlling concentration of carbon dioxide in the gas headspace to a preselected value through the addition of carbon dioxide to the enclosure; and b. controlling gas pressure inside the enclosure within a range from about 2 to about 6 inches of water by venting or adding gas through at least one of the plurality of ports.

* * * * *